US005798441A

United States Patent [19]

Cormier et al.

[11] Patent Number: 5,798,441

[45] Date of Patent: Aug. 25, 1998

[54] RECOMBINANT DNA VECTORS CAPABLE OF EXPRESSING APOAEQUORIN

[75] Inventors: Milton J. Cormier, Bogart, Ga.; Douglas Prasher, East Falmouth, Mass.

[73] Assignee: University of Georgia Research Foundation, Inc., Athens, Ga.

[21] Appl. No.: 346,379

[22] Filed: Nov. 29, 1994

Related U.S. Application Data

[63] Continuation of Ser. No. 960,195, Oct. 9, 1992, Pat. No. 5,422,266, which is a continuation of Ser. No. 569,362, Aug. 13, 1990, abandoned, which is a continuation of Ser. No. 165,422, Feb. 29, 1988, abandoned, which is a continuation of Ser. No. 942,273, Dec. 15, 1986, abandoned, which is a continuation-in-part of Ser. No. 687,903, Dec. 31, 1984, abandoned.

[51] Int. Cl.$^6$ .......... C07K 14/435

[52] U.S. Cl. .......... 530/324; 530/350

[58] Field of Search .......... 530/350, 324; 455/69.1, 172.3, 252.3–252.35, 320.1, 10, 11, 72–75; 536/23.2, 23.5, 23.4

[56] References Cited

U.S. PATENT DOCUMENTS

| | | | |
|---|---|---|---|
| 4,011,219 | 3/1977 | Nishii et al. | 544/237 |
| 4,104,029 | 8/1978 | Maier, Jr. | 435/7.4 |
| 4,160,016 | 7/1979 | Ullman | 436/537 |
| 4,181,650 | 1/1980 | Maier et al. | 530/303 |
| 4,220,450 | 9/1980 | Maggio | 436/537 |
| 4,225,485 | 9/1980 | Buckler et al. | 530/391.5 |
| 4,331,808 | 5/1982 | Buckler et al. | 544/234 |
| 4,334,069 | 6/1982 | Buckler et al. | 544/237 |
| 4,380,580 | 4/1983 | Boguslaski et al. | 435/5 |
| 4,396,579 | 8/1983 | Schroeder et al. | 422/52 |
| 4,478,817 | 10/1984 | Campbell et al. | 424/7.1 |
| 4,581,335 | 4/1986 | Baldwin | 435/172.3 |
| 4,604,364 | 8/1986 | Kosak | 436/501 |
| 4,614,712 | 9/1986 | Baldwin et al. | 435/7.92 |
| 4,665,022 | 5/1987 | Schaeffer et al. | 435/7.72 |
| 4,740,468 | 4/1988 | Weng et al. | 435/7.91 |
| 4,968,613 | 11/1990 | Matsuda | 435/172.3 |
| 5,162,227 | 11/1992 | Cormier | 435/252.33 |

FOREIGN PATENT DOCUMENTS

| | | |
|---|---|---|
| 1461877 | 1/1977 | United Kingdom . |
| 2 095 830 | 6/1982 | United Kingdom . |
| 81 01883 | 9/1981 | WIPO . |
| 87 03304 | 4/1987 | WIPO . |
| 89 09393 | 5/1989 | WIPO . |

OTHER PUBLICATIONS

Prasher, D.C. et al., "Cloning and Expression of the cDNA Coding for Aequorin, a Bioluminescent Calcium–Binding Protein," *Biochemical and Biophysical Research Communications*, vol. 126, No.3, pp. 1259–1268, (Feb. 15, 1985).

Ward, W.W. et al., "Extraction of Renilla–type luciferin from the calcium–activated photoproteins aequorin, mnemiopsin, and berovin," *Proc. Natl. Acad. Sci. USA*, vol. 72, No. 7, pp. 2530–2534, (Jul. 1975).

Maniatis, T. et al., "Molecular Cloning: A Laboratory Manual, ," Cold Spring Harbor Laboratory, pp. 224–246 and 416–427, (1982).

Lehninger, A., *Biochemistry*, Worth Publishers, New York, p. 718, (1970).

Lehninger, *Biochemistry*, Woth Publishers, New York, pp. 69–71 (1970).

Prasher et al., "Cloning and Expression of the cDNA Coding for Aequorin, A Bioluminescent Calcium–Binding Protein," *Biochem. Biophys. Res. Comm.*, vol. 126, No. 3, pp. 1259–1268 (1985).

Inouye, S. et al., "Expression of Apoaequorin Complementary DNA in *Escherichia coli*," *Biochemistry*, vol. 25, No. 26, pp. 8425–8429, (Dec. 30, 1986).

Inouye, S., et al., "Cloning and sequence analysis of cDNA for the luminescent protein aequorin," *Proc. Natl. Acad. Sci. USA*, vol. 82, pp. 3154–3158, (May 1985).

Tsuji, F.I. et al., "Site–specific mutagenesis of the calcium–binding photoprotein aequorin," *Proc. Natl. Acad. Sci. USA*, vol. 83, pp. 8107–8111, (Nov. 1986).

Charbonneau, H. et al., "Amino Acid Sequence of the Calcium–Dependent Photoprotein Aequorin," *Biochemistry*, vol. 24, No. 24, pp. 6762–6771, (Nov. 19, 1985).

Shimomura, O. et al., "Resistivity to denaturation of the apoprotein of aequorin and reconstitution of the luminescent photoprotein from the partially denatured apoprotein," *Biochem. J.*, vol. 199, pp. 825–828, (Dec. 1981).

Prendergast, F.G. et al., "Chemical and Physical Properties of Aequorea and the Green Fluorescent Protein Isolated from *Aequorin forskalea*," *Biochemistry*, vol. 17, No. 17, pp. 3448–3453, (Aug. 1978).

Shimomura, O. et al., "Chemical Nature of Bioluminescence Systems in Coelenterates," *Proc. Natl. Acad. Sci. USA*, vol. 72, No. 4, pp. 1546–1549, (Apr. 1975).

Muesing, M. et al., "High–level expression in *Escherichia coli* of calcium–binding domains of an embryonic sea urchin protein," *Gene*, vol. 1108, pp. 155–164, (Nov. 1984).

Ohno, S. et al., "Evolutionary origin of a calcium–dependent protease by fusion of genes for a thiol protease and a calcium–binding protein? " *Nature*, vol. 312, No. 6, pp. 566–570, (Dec. 1984).

Kuwano, R. et al., "Molecular cloning and the complete nucleotide sequence of cDNA to mRNA for S–100 protein of rat brain," *Nucleic Acids Research*, vol. 12, No. 19, pp. 7455–7456, (1984).

Putkey, J.A. et al., "Chicken Calmodulin Genes," *The Journal of Biological Chemistry*, vol. 258, No.19, pp. 11864–11870, (Oct. 10, 1983).

Inouye, S. et al., "Structural similarities between the development–specific protein S from a Gram–negative bacterium, *Myxococcus xanthus*, and calmodulin," *Proc. Natl. Acad. Sci. USA*, vol. 80, pp. 6829–6833, (Nov. 1983).

(List continued on next page.)

*Primary Examiner*—James Martinell
*Attorney, Agent, or Firm*—Jones & Askew

[57] ABSTRACT

A gene which codes for the protein apoaequorin is disclosed along with recombinant DNA vectors containing this gene. Homogeneous peptides having the bioluminescence properties of natural, mixed apoaeqorin are also disclosed.

2 Claims, 4 Drawing Sheets

OTHER PUBLICATIONS

Garfinkel, L.L. et al., "Cloning and Characterization of cDNA Sequences Corresponding to Myosin Light Chains 1, 2, and 3, Troponin–C, Troponin–T, α–Tropomyosin, andαActin," *The Journal of Biological Chemistry*, vol. 257, No. 18, pp. 11078–11086, (Sep. 25, 1982).

Suggs, S.V. et al., "Use of synthetic oligonucleotides as hybridization probes: Isolation of cloned cDNA sequences for human $\beta_2$–microglobulin," *Proc. Natl. Acad. Sci. USA*, vol. 78, No. 11, pp. 6613–6617, (Nov. 1981).

Sanger, F. et al., "Nucleotide Sequence of Bacteriophage λ DNA," *J. Mol. Biol.*, vol. 162, pp. 729–739, (1982).

Chen, R., "Complete amino acid sequence and glycosylation sites of glycoprotein gp71A of Friend murine leukemia virus," *Proc. Natl. Acad. Sci. USA*, vol. 79, pp. 5788–5792, (Oct. 1982).

Patel, A. et al., "Calcium–Sensitive Photoproteins as Bioluminescent Labels in Immunoassay," *Analytical Applications of Bioluminescence and Chemiluminescence*, pp. 273–276, (1984).

Cummings, R.D. et al., "A Mouse Lymphoma Cell Line Resistant to the Leukoagglutinating Lectin from *Phaseolus vulgaris* Is Deficient in UDP–GlcNAc:α–D–mannoside β1,6 N–Acetylglucosaminyltransferase," *The Journal of Biological Chemistry*, vol. 257, No. 22, pp. 13421–13427, (Nov. 25, 1982).

Stephenson, D.G. et al., "Studies of the Luminescent Response of the $Ca^{2+}$–Activated Photoprotein, Obelin," *Biochimica et Biophysica Acta*, vol. 678, pp. 65–75, (1981).

Cormier, M.J., "Renilla and Aequorin Bioluminescence," *Bioluminescence and Chemiluminescence*, pp. 225–233, (1985).

Cormier, M.J., "Mechanism of energy conversion and transfer in bioluminescence," *Chemical Abstract*, vol. 93, No. 5, p. 545, No. 4201H, (Aug. 4, 1980).

DeLuca, M.A., "Bioluminescence and Chemiluminescence," *Methods in Enzymology*, vol. LVII, pp. 228, 240, 242, 243, 590 (1978).

Hart, R.C. et al., "Mechanism of the Enzyme–Catalyzed Bioluminescent Oxidation of Coelenterate–Type Luciferin," *Biochemical and Biophysical Research Communications*, vol. 81, No. 3, pp. 980–986, (Apr. 14, 1978).

Matthews, J.C. et al., "Purification and Propeties of *Renilla reniformis* Luciferase," *Biochemistry*, vol. 16, No. 1, pp. 85–91, (1977).

Hart, R.C. et al., "*Renilla reniformis* Bioluminescence: Luciferase–Catalyzed Production of Nonradiating Excited States from Luciferin Analogues and Elucidation of the Excited State Species Involved in Energy Transfer to Renilla Green Fluorescent Protein," *Biochemistry*, vol. 18, No. 11, pp. 2204–2210, (1979).

Hori, K. et al., "Structure of native *Renilla reniformis* luciferin," *Proc. Natl. Acad. Sci. USA*, vol. 74, No. 10, pp. 4285–4287, (Oct. 1977).

Anderson, J.M. et al., "Lumisomes: A Bioluminescent Particle Isolated from the Sea Pansy *Renilla reniformis*," *Chemiluminescence and Bioluminescence*, Plenum Publishing Corporation, pp. 387–392, (1973).

Cormier, M.J., "Comparative Biochemistry of Animal Systems," *Bioluminescence In Action*, Academic Press, p. 75–108, (1978).

Cormier, M.J. et al., "Evidence for Similar biochemical Requirements for Bioluminescence among the Coelenterates," *Journal of Cellular Physiology*, vol. 81, No. 2, pp. 291–297, (Apr. 1973).

Patel, A. et al., "A new chemiluminescent label for use in immunoassay," *Biochemical Society Transactions*, vol. 10, pp. 224–225, (1982).

Oi, V.T. et al., "Fluorescent Phycobiliprotein Conjugates for Analyses of Cells and Molecules," *The Journal of Cell Biology*, vol. 93, pp. 981–986, (Jun. 1982).

Simpson, J.S.A. et al., "A stable chemiluminescent–labelled antibody for immunological assays," *Nature*, vol. 279, No. 14, pp. 646–647, (Jun. 1979).

Pazzagli, G.F. et al., "Homogeneous Luminescent Immunoassay for Progesterone: A study on the Antibody–Enhanced Chemiluminescence," *Luminescent Assays: Perspectives in Endocrinology and Clinical Chemistry*, Raven Press, pp. 191–200, (1982).

Kim, J.B. et al., "Measurement of Plasma Estradiol–17β by Solid–Phase Chemiluminescence Immunoassay," *Clinical Chemistry*, vol. 28, No. 5, pp. 1120–1124, (1982).

Kohen, F. et al., "An Immunoassay for Plasma Cortisol Based on Chemiluminescence," *Steroids*, pp. 421–437, (May 21, 1980).

Kohen, F. et al., "An Assay Procedure for Plasma Progesterone Based on Antibody–Enhanced Chemiluminescence," *FEBS Letters*, vol. 104, No. 1, pp. 201–205, (Aug. 1979).

Jaye, M. et al., "Isolation of a human anti –haemophilic factor IX cDNA clone using a unique 52–base synthetic oligonucleotide probe deduced from the amino acid sequence of bovine factor IX," *Nucleic Acids Research*, vol. 11, No. 8, pp. 2325–2335, (1983).

Hsu, S., "Immunoperoxidase Techniques Using the Avidin––Biotin System," *Department of Pathology and Laboratory Medicine, University of Texas Health Science Center*, pp. 467–476, (1985).

Matsuda, G. et al., "The Primary Structure of L–1 Light Chain of Chicken Fast Skeletal Muscle Myosin and Its Genetic Implication," *FEBS Letters*, vol. 126, No. 1, pp. 111–113, (Apr. 1981).

Pierce, M. et al., "The Localization of Galactosyltransferases in Polyacrylamide Gels by a Coupled Enzyme Assay," *Analytical Biochemistry*, vol. 102, pp. 441–449, (1980).

Smith, D.F. et al., "Rabbit Antibodies against the Human Milk Sialyloligosaccharide Alditol of LS–Tetrasaccharide a(NeuAcα2–3Galβ1–3GlcNAcβ1–4$Glc_{OH}$)," *Archives of Biochemistry and Biophysics*, vol. 241, No. 1, pp. 298–303, (Aug. 15, 1985).

Lorenz, W.W. et al., "Isolation and Expression of cDNA Encoding *Renilla reniformis* luciferase," *Proc. Natl. Acad. Sci. USA*, vol. 88, pp. 4438–4442, (May 1991).

Blinks, J.R. et al., "Practical Aspects of the Use of Aequorin as a Calcium Indicator: Assay, Preparation, Microinjection, and Interpretation of Signals," *Methods of Enzymology*, vol. 57, pp. 292–328, (1978).

Miyata, T. et al., "Plasminogens Tochigi II and Nagoya: Two Additional Molecular Defects with Ala–600—Thr Replacement Found in Plasmin Light Chain Variants," *J. Biochem.*, vol. 96, No. 2, pp. 277–285, (Aug. 1984).

Cormier, M.J., et al., "Bioluminescence: Recent Advances," *Annual Review of Biochemistry*, vol. 44, pp. 255–271, (1975).
Prasher, D.C. et al., "Sequence Comparisons of cDNAs Encoding for Aequorin Isotypes," *Department of Biochemistry, University of Georgia*, (1987).
Cormier, M.J. et al., "Cloning of the Apoaequorin cDNA and Its Expression in *E. coli*," *Report to Roche Diagnostics*, (Oct. 26, 1984).
Erwin et al., *Biochemistry*, vol. 22, p. 4856 (1983).
Wallace et al., *Nucleic Acids Res.*, vol. 6, p. 3543 (1979).
Kohama et al. Biochemistry 10: 4149 (1971).

RECOMBINANT DNA VECTORS CAPABLE OF EXPRESSING APOAEQUORIN

This application is a continuation of U.S. patent application Ser. No. 07/960,195, filed Oct. 9, 1992, now U.S. Pat. No. 5,422,266, which is a continuation of U.S. patent application Ser. No. 07/569,362, filed Aug. 13, 1990, abandoned, which is a continuation of U.S. patent application Ser. No. 07/165,422, filed Feb. 29, 1988, abandoned, which is a continuation of Ser. No. 06/942,273, filed Dec. 15, 1986, abandoned, which is a continuation-in-part of U.S. patent application Ser. No. 06/687,903, filed Dec. 31, 1984 abandoned.

BACKGROUND OF THE INVENTION

1. Field of the Invention

This invention relates to the field of genetic engineering and more particularly to the insertion of genes for the protein apoaequorin into recombinant DNA vectors and to the production of apoaequorin in recipient strains of microorganisms.

2. Description of the Background

Apoaequorin is a single polypeptide chain protein which can be isolated from the luminous jellyfish *Aequorea victoria*. When this protein contains one molecule of coelenterate luciferin bound non-covalently to it, it is known as aequorin. Aequorin is oxidized in the presence of calcium ions to produce visible light. Once light is produced, the spent protein (apoaequorin) can be purified from the oxidized luciferin and subsequently recharged using natural or synthetic luciferin under appropriate conditions. The addition of calcium ions to the recharged aequorin will again result in the production of light. Apoaequorin can therefore be used in various chemical and biochemical assays as a marker.

Natural apoaequorin is not a single compound but rather represents a mixture of molecular species. When pure natural aequorin, representing that of many thousands of individual Aequorea, is subjected to electrophoresis (O. Gabriel, *Methods Enzymol.* (1971) 22:565–578) in alkaline buffers under non-denaturing conditions, including 0.1 mM EDTA in all buffers, at least six distinct bands of blue luminescence are visible when the gel (0.5 cm×10 cm) is immersed in 0.1M $CaI_2$. This observation agrees with that of J. R. Blinks and G. C. Harres (Fed. Proc. (1975) 34:474) who observed as many as twelve luminescent bands after the isoelectric focusing of a similar extract. Blinks and Harres observed more species because isoelectric focusing is capable of higher resolution than is electrophoresis. However, none of the bands was ever isolated as a pure peptide.

Furthermore, it is difficult to produce sufficient aequorin or apoaequorin from jellyfish or other natural sources to provide the amounts necessary for use in bioluminescence assays. Accordingly, an improved means for producing apoaequorinin sufficient quantities for commercial utilization is greatly needed.

Recently developed techniques have made it possible to employ microorganisms, capable of rapid and abundant growth, for the synthesis of commercially useful proteins and peptides, regardless of their source in nature. These techniques make it possible to genetically endow a suitable microorganism with the ability to synthesize a protein or peptide normally made by another organism. The technique makes use of a fundamental relationship which exists in all living organisms between the genetic material, usually DNA, and the proteins synthesized by the organism. This relationship is such that the amino acid sequence of the protein is reflected in the nucleotide sequence of the DNA. There are one or more trinucleotide sequence groups specifically related to each of the twenty amino acids most commonly occuring in proteins. The specific relationship between each given trinucleotide sequence and its corresponding amino acid constitutes the genetic code. The genetic code is believed to be the same or similar for all living organisms. As a consequence, the amino acid sequence of every protein or peptide is reflected by a corresponding nucleotide sequence, according to a well understood relationship. Furthermore, this sequence of nucleotides can, in principle, be translated by any living organism.

TABLE 1

GENETIC CODE

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter triplet represents a trinucleotide of DNA having a 5' end on the left and a 3' end on the right. The letters stand for the purine or pyrimidine bases forming the nucleotide sequence.
A = adenine
G = guanine
C = cytosine
J = A or G
K = T or C
L = A, T, C, or G
M = A, C, or T
T = Thymine
X = T or C if Y is A or G
X = C if Y is C or T
Y = A, G, C, or T if X is C
Y = A or G if X is T
W = C or A if Z is C or T
W = C if Z is C or T
Z = A, G, C, or T if W is G
Z = A or G if W is A
QR = TC if S is A, G, C, or T
QR = AG if S is T or C
S = A, G, C, or T if QR is TC
S = T or C if QR is AG The trinucleotides of Table 1, termed codons, are presented as DNA trinucleotides, as they exist in the genetic material of a living organism. Expression of these codons in protein synthesis requires intermediate formation of messenger RNA (mRNA), as described more fully, infra. The mRNA codons have the same sequences as the DNA codons of Table 1, except that uracil is found in place of thymine. Complementary trinucleotide DNA sequences having opposite strand polarity are functionally equivalent to the codons of Table 1, as is understood in the art. An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they can result in the production of the same amino acid sequence in all organisms, although certain strains may translate some sequences more efficiently than they do others. Occasionally, a methylated variant of a purine or pyrimidine may be found in a given nucleotide sequence. Such methylations do not affect the coding relationship in any way.

It its basic outline, a method of endowing a microorganism with the ability to synthesize a new protein involves three general steps: (1) isolation and purification (or chemical synthesis) of the specific gene or nucleotide sequence containing the genetically coded information for the amino acid sequence of the desired protein, (2) recombination of the isolated nucleotide sequence with an appropriate vector, typically the DNA of a bacteriophage or plasmid, and (3) transfer of the vector to the appropriate microorganism and selection of a strain of the recipient microorganism containing the desired genetic information.

A fundamental difficulty encountered in attempts to exploit commercially the above-described process lies in the first step, the isolation and purification of the desired specific genetic information. DNA exists in all living cells in the form of extremely high molecular weight chains of nucleotides. A cell may contain more than 10,000 structural genes, coding for the amino acid sequences of over 10,000 specific proteins, each gene having a sequence many hundreds of nucleotides in length. For the most part, four different nucleotide bases make up all the existing sequences. These are adenine (A), guanine (G), cytosine (C), and thymine (T). The long sequences comprising the structural genes of specific proteins are consequently very similar in overall chemical composition and physical properties. The separation of one such sequence from the plethora of other sequences present in isolated DNA cannot ordinarily be accomplished by conventional physical and chemical preparative methods.

Two general methods have been used in the prior art to accomplish step (1) in the above-described general procedure. The first method is sometimes referred to as the shotgun technique. The DNA of an organism is fragmented into segments generally longer than the desired nucleotide sequence. Step (1) of the above-described process is essentially by-passed. The DNA fragments are immediately recombined with the desired vector, without prior purification of specific sequences. Optionally, a crude fractionation step may be interposed. The selection techniques of microbial genetics are relied upon to select, from among all the possibilities, a strain of microorganism containing the desired genetic information. The shotgun procedure suffers from two major disadvantages. More importantly, the procedure can result in the transfer of hundreds of unknown genes into recipient microorganisms, so that during the experiment, new strains are created, having unknown genetic capabilities. Therefore, the use of such a procedure could create a hazard for laboratory workers and for the environment. A second disadvantage of the shotgun method is that it is extremely inefficient for the production of the desired strain, and is dependent upon the use of a selection technique having sufficient resolution to compensate for the lack of fractionation in the first step. However, methods of overcoming these disadvantages exist, as will become apparent in later sections of this application.

The second general method takes advantage of the fact that the total genetic information in a cell is seldom, if ever, expressed at any given time. In particular, the differentiated tissues of higher organisms may be synthesizing only a minor portion of the proteins which the organism is capable of making at any one time. In extreme cases, such cells may be synthesizing predominantly one protein. In such extreme cases, it has been possible to isolate the nucleotide sequence coding for the protein in question by isolating the corresponding messenger RNA from the appropriate cells.

Messenger RNA functions in the process of converting the nucleotide sequence information of DNA into the amino acid sequence structure of a protein. In the first step of this process, termed transcription, a local segment of DNA having a nucleotide sequence which specifies a protein to be made, is copied into RNA. RNA is a polynucleotide similar to DNA except that ribose is substituted for deoxyribose and uracil is used in place of thymine. The nucleotide bases in RNA are capable of entering into the same kind of base pairing relationships that are known to exist between the complementary strands of DNA. A and U (T) are complementary, and G and C are complementary. The RNA transcript of a DNA nucleotide sequence will be complementary to the copied sequence. Such RNA is termed messenger RNA (mRNA) because of its status as intermediary between the genetic apparatus of the cell and its protein synthesizingd apparatus. Generally, the only mRNA sequences present in the cell at any given time are those which correspond to proteins being actively synthesized at that time. Therefore, a differentiated cell whose function is devoted primarily to the synthesis of a single protein will contain primarily the RNA species corresponding to that protein. In those instances where it is feasible, the isolation and purification of the appropriate nucleotide sequence coding for a given protein can be accomplished by taking advantage of the specialized synthesis of such protein in differentiated cells.

A major disadvantage of the foregoing procedure is that it is applicable only in the relatively rare instances where cells can be found engaged in synthesizing primarily a single protein. The majority of proteins of commercial interest are not synthesized in such a specialized way. The desired proteins may be one of a hundred or so different proteins being produced by the cells of a tissue or organism at a given time. Nevertheless, the mRNA isolation technique is useful since the set of RNA species present in the cell usually represents only a fraction of the total sequences existing in the DNA, and thus provides an initial purification.

In a more recent development, U.S. Pat. No. 4,363,877 provides a process whereby nucleotide sequences can be isolated and purified even when present at a frequency as low as 2% of a heterogeneous population of mRNA sequences. Furthermore, the method may be combined with known methods of fractionating mRNA to isolate and purify sequences present in even lower frequency in the total RNA population as initially isolated. The method is generally applicable to mRNA species extracted from virtually any organism and therefore provides a powerful basic tool for the ultimate production of proteins of commercial and research interest, in useful quantities.

The process takes advantage of certain structural features of mRNA and DNA, and makes use of certain enzyme catalyzed reactions. The nature of these reactions and structural details as they are understood in the prior art are described herein and are further detailed in the patent. The symbols and abbreviations used herein are set forth in the following table.

TABLE 2

| | |
|---|---|
| DNA — deoxyribonucleic acid | A — Adenine |
| RNA — ribonucleic acid | T — Thymine |
| cDNA — complementary DNA (enzymatically synthesized from an mRNA sequence) | G — Guanine |
| | C — Cytosine |
| | U — Uracil |
| mRNA — messenger RNA | Tris — 2-Amino-2-hydroxymethyl-1,3-propanediol |
| dATP — deoxyadenosine triphosphate | |
| dGTP — deoxyguanosine triphosphate | |
| dCTP — deoxycytidine triphosphate | EDTA — ethylenediamine tetra-acetic acid |
| TCA — Trichloroacetic acid | |
| dTTP — thymidine triphosphate | |
| | ATP — adenosine triphosphate |

In its native configuration, DNA exists in the form of paired linear polynucleotide strands. The complementary base pairing relationships described above exist between the paired strands such that each nucleotide base of one strand exists opposite its complement on the other strand. The entire sequence of one strand is mirrored by a complementary sequence on the other strand. If the strands are separate, it is possible to synthesize a new partner strand, starting from the appropriate precursor monomers. The sequence of addition of the monomers starting from one end is determined by, and complementary to, the sequence of the original intact polynucleotide strand, which thus serves as a template for the synthesis of this complementary partner. The synthesis of mRNA corresponding to a specific nucleotide sequence of DNA is understood to follow the same basic principle. Therefore a specific mRNA molecule will have a sequence complementary to one strand of DNA and identical to the sequence of the opposite DNA strand, in the region transcribed. Enzymatic mechanisms exist within living cells which permit the selective transcription of a particular DNA segment containing the nucleotide sequence for a particular protein. Consequently, isolating the mRNA which contains the nucleotide sequence coding for the amino acid sequence of a particular protein is equivalent to the isolation of the same sequence, or gene, from the DNA itself. If the mRNA is retranscribed to form DNA complementary thereto (cDNA), the exact DNA sequence is thereby reconstituted and can, by appropriate techniques, be inserted into the genetic material of another organism. The two complementary versions of a given sequence are therefore inter-convertible and functionally equivalent to each other.

The nucleotide subunits of DNA and RNA are linked together by phosphodiester bonds between the 5' position of one nucleotide sugar and the 3' position of its next neighbor. Reiteration of such linkages produces a linear polynucleotide which has polarity in the sense that one end can be distinguished from the other. The 3' end may have a free 3'-hydroxyl, or the hydroxyl may be substituted with a phosphate or a more complex structure. The same is true of the 5' end. In eucaryotic organisms, i.e., those having a defined nucleus and mitotic apparatus, the synthesis of functional mRNA usually includes the addition of polyadenylic acid to the 3' end of the mRNA. Messenger RNA can therefore be separated from other classes of RNA isolated from an eucaryotic organism by column chromatography on cellulose to which is attached polythymidylic acid. See Aviv and Leder, *Proc. Natl. Acad. Sci. USA,* (1972) 69:1408. Other chromatographic methods, exploiting the base-pairing affinity of poly A for chromatographic packing materials, containing oligo dT, poly U, or combinations of poly T and poly U, for example, poly U-Sepharose, are likewise suitable.

Reverse transcriptase catalyzes the synthesis of DNA complementary to an RNA template strand in the presence of the RNA template, a primer which may be any complementary oligo or polynucleotide having a 3'-hydroxyl, and the four deoxynucleotide triphosphates, dATP, dGTP, dCTP, and dTTP. The reaction is initiated by the non-covalent association of the oligodeoxynucleotide primer near the 3' end of mRNA followed by stepwise addition of the appropriate deoxynucleotides, as determined by base-pairing relationships with the mRNA nucleotide sequence, to the 3' end of the growing chain. The product molecule may be described as a hairpin structure in which the original RNA is paired by hydrogen bonding with a complementary strand of DNA partly folded back upon itself at one end. The DNA and RNA strands are not covalently joined to each other. Reverse transcriptase is also capable of catalyzing a similar reaction using a single-stranded DNA template, in which case the resulting product is a double-stranded DNA hairpin having a loop of single-stranded, DNA joining one set of ends. See Aviv and Leder, *Proc. Natl. Acad. Sci. USA* (1972) 69:1408 and Efstratiadis, Kafatos, Maxam, and Maniatis, *Cell* (1976) 7:279.

Restriction endonucleases are enzymes capable of hydrolyzing phosphodiester bonds in DNA, thereby creating a break in the continuity of the DNA strand. If the DNA is in the form of a closed loop, the loop is converted to a linear structure. The principal feature of a restriction enzyme is that its hydrolytic action is exerted only at a point where a specific nucleotide sequence occurs. Such a sequence is termed the restriction site for the restriction endonuclease. Restriction endonucleases from a variety of sources have been isolated and characterized in terms of the nucleotide sequence of their restriction sites. When acting on double-stranded DNA, some restriction endonucleases hydrolyze the phosphodiester bonds on both strands at the same point, producing blunt ends. Others catalyze hydrolysis of bonds separated by a few nucleotides from each other, producing free single-stranded regions at each end of the cleaved molecule. Such single-stranded ends are self-complementary, hence cohesive, and may be used to rejoin the hydrolyzed DNA. Since any DNA susceptible to cleavage by such an enzyme must contain the same recognition site, the same cohesive ends will be produced, so that it is possible to join heterogeneous sequences of DNA which have been treated with restriction endonuclease to other sequences similarly treated. See Roberts, *Crit. Rev. Biochem.* (1976) 4:123.

It has been observed that restriction sites for a given enzyme are relatively rare and are nonuniformly distributed. Whether a specific restriction site exists within a given segment is a matter which must be empirically determined. However, there is a large and growing number of restriction endonucleases, isolated from a variety of sources with varied site specificity, so that there is a reasonable probability that a given segment of a thousand nucleotides will contain one or more restriction sites.

For general background see Watson, J. D., *The Molecular Biology of the Gene,* 3d Ed., Benjamin, Menlo Park, Calif., (1976); Davidson, J. N., *The Biochemistry of the Nucleic Acids,* 8th Ed., Revised by Adams, R. L. P., Burdon, R. H., Campbell, A. M. and Smellie, R. M. S., Academic Press, New York, (1976); and Hayes, W., *The Genetics of Bacteria and Their Viruses, Studies in Basic Genetics and Molecular Biology,* 2d Ed., Blackwell Scientific Pub., Oxford (1968).

SUMMARY OF THE INVENTION

Accordingly, it is an object of this invention to provide a microorganism capable of providing useful quantities of apoaequorin.

It is a further object of this invention to provide a recombinant DNA vector capable of being inserted into a microorganism and expressing apoaequorin.

It is still another object of this invention to provide a DNA segment of defined structure that can be produced synthetically or isolated from natural sources and that can be used in the production of the desired recombinant DNA vectors.

It is yet another object of this invention to provide a peptide that can be produced synthetically in a laboratory or by microorganism that will mimic the activity of natural apoaequorin.

These and other objects of the invention as will hereinafter become more readily apparent have been accomplished by providing a homogeneous pepetide selected from (1) compounds of (a) a first formula

V K L T P D F D N P K W I G R H K H M F N F L D V

N H N G R I S L D E M V Y K A S D I V I N N L G A

T P E Q A K R H K D A V E A F F G G A G M K Y G V

E T E W P E Y I E G W K R L A S E E L K R Y S K N

Q I T L I R L W G D A L F D I I D K D Q N G A I S

L D E W K A Y T K S D G I I Q S S E D C E E T F R

V C D I D E S G Q L D V D E M T R Q H L G F W Y T

M D P A C E K L Y G G A V P-COOH wherein A is alanine, C is cysteine, D is aspartate, E is glutamate, F is phenylalanine, G is glycine, H is histidine, I is isoleucine, K is lysine, L is leucine, M is methicnine, N is asparagine, P is proline, Q is glutamine, R is arginine, S is serine, T is threonine, V is valine, W is tryptonphan, and Y is tyrosine, (b) a second formula in which $P_5$ is replaced by S, $D_8$ is replaced by D, $K_{11}$ is replaced by R, $R_{30}$ is replaced by K, $E_{63}$ is replaced by G, $A_{64}$ is replaced by D, $E_{78}$ is replaced by D, $E_{81}$ is replaced by A, $R_{88}$ is replaced by K, $S_{91}$ is replaced by T, $E_{92}$ is replaced by C or D, $K_{95}$ is replaced by E, $R_{96}$ is replaced by K, $S_{98}$ is replaced by A, $Q_{101}$ is replaced by E, $I_{102}$ is replaced by P, $L_{107}$ is replaced by I, $I_{116}$ is replaced by V, $S_{125}$ is replaced by T, $S_{135}$ is replaced by A, $S_{141}$ is replaced by T, or $S_{157}$ is replace by N in said first formula wherein subscript numbers refer to the amino acid position numbered from the amino terminal of said first formula, (c) a third formula in which from 1 to 15 amino acids are absent from either the amino terminal, the carboxy terminal, or both terminals of said first formular or said second formula, or (d) a fourth formula in which from 1 to 10 additional amino acids are attached sequentially to the amino terminal, carboxy terminal, or both terminals of said first formula or said second formula and (2) salts of compounds having said formulas, wherein said peptide is capable of binding coelenterate luciferin and emitting light in the presence of $Ca^{2+}$.

DNA molecules, recombinant DNA vectors, and modified microorganisms comprising a nucleotide sequence $GTL_1$ $AAJ_2$ $XTY_3$ $ACL_4$ $[CCL\ or\ QRS]_5$ $GAK_6$ $TTK_7$ $[GAK\ or\ AAK]_8$ $AAK_9$ $CCL_{10}$ $[AAJ\ or\ WGZ]_{11}$ $TGG_{12}$ $ATM_{13}$ $GGL_{14}$ $WGZ_{15}$ $CAK_{16}$ $AAJ_{17}$ $CAK_{18}$ $ATG_{19}$ $TTK_{20}$ $AAK_{21}$ $TTK_{22}$ $XTY_{23}$ $GAK_{24}$ $GTL_{25}$ $AAK_{26}$ $CAK_{27}$ $AAK_{28}$ $GGL_{29}$ $[WGJ\ or$ $AAJ]_{30}$ $ATM_{31}$ $QRS_{32}$ $XTY_{33}$ $GAK_{34}$ $GAJ_{35}$ $ATG_{36}$ $GTL_{37}$ $TAK_{38}$ $AAJ_{39}$ $GCL_{40}$ $QRS_{41}$ $GAK_{42}$ $ATM_{43}$ $GTL_{44}$ $ATM_{45}$ $AAK_{46}$ $AAK_{47}$ $XTY_{48}$ $GGL_{49}$ $GCL_{50}$ $ACL_{51}$ $CCL_{52}$ $GAJ_{53}$ $CCJ_{54}$ $GCL_{55}$ $AAJ_{56}$ $WGZ_{57}$ $CAK_{58}$ $AAJ_{59}$ $GAK_{60}$ $GCL_{61}$ $GTL_{62}$ $[GAJ\ or\ GGL]_{63}$ $[GCL$ -continued $or\ GAK]_{64}$ $TTK_{65}$ $TTK_{66}$ $GGL_{67}$ $GGL_{68}$ $GCL_{69}$ $GGL_{70}$ $ATG_{71}$ $AAJ_{72}$ $TAK_{73}$ $GGL_{74}$ $GTL_{75}$ $GAJ_{76}$ $ACL_{77}$ $[GAJ\ or\ GAK]_{78}$ $TGG_{79}$ $CCL_{80}$ $[GAJ\ or\ GCL]_{81}$ $TAK_{82}$ $ATM_{83}$ $GAJ_{84}$ $GGL_{85}$ $TGG_{86}$ $AAJ_{87}$ $[WGZ\ or\ AAJ]_{88}$ $XTY_{89}$ $GCL_{90}$ $[QRS\ or\ ACL]_{91}$ $[GAJ,$ $TGK,\ or\ GAK]_{92}$ $GAJ_{93}$ $XTY_{94}$ $[AAJ\ or\ GAJ]_{95}$ $[WGZ\ or$ $AAJ]_{96}$ $TAK_{97}$ $[QRS\ or\ GCL]_{98}$ $AAJ_{99}$ $AAK_{100}$ $[CAJ\ or$ $GAJ]_{101}$ $[ATM\ ro\ CCL]_{102}$ $ACL_{103}$ $XTY_{104}$ $ATM_{105}$ $WGZ_{106}$ $[XTY\ or\ ATM]_{107}$ $TGG_{108}$ $GGL_{109}$ $GAK_{110}$ $GCL_{111}$ $XTY_{112}$ $TTK_{113}$ $GAK_{114}$ $ATM_{115}$ $[ATM\ or\ GTL]_{116}$ $GAK_{117}$ $AAJ_{118}$ $GAK_{119}$ $CAJ_{120}$ $AAK_{121}$ $GGL_{122}$ $GCL_{123}$ $ATM_{124}$ $[QRS\ or$ $ACL]_{125}$ $XTY_{126}$ $[GAK]_{127}$ $GAJ_{128}$ $TGG_{129}$ $AAJ_{130}$ $GCL_{131}$ $TAK_{132}$ $ACL_{133}$ $AAJ_{134}$ $[QRS\ or\ GCL]_{135}$ $GAK_{136}$ $GGL_{137}$ $ATM_{138}$ $ATM_{139}$ $CAJ_{140}$ $[QRS\ or\ ACL]_{141}$ $QRS_{142}$ $GAJ_{143}$ $[GAK]_{144}$ $TGK_{145}$ $GAJ_{146}$ $GAJ_{147}$ $ACL_{148}$ $TTK_{149}$ $WGZ_{150}$ $GTL_{151}$ $TGK_{152}$ $GAK_{153}$ $ATM_{154}$ $GAK_{155}$ $GAJ_{156}$ $[QRS\ or\ AAK]_{157}$ $GGL_{158}$ $CAJ_{159}$ $XTY_{160}$ $GAK_{161}$ $GTL_{162}$ $GAK_{163}$ $GAJ_{164}$ $ATG_{165}$ $ACL_{166}$ $WGZ_{167}$ $CAJ_{168}$ $CAK_{169}$ $XTY_{170}$ $GGL_{171}$ $TTK_{172}$ $TGG_{173}$ $TAK_{174}$ $ACL_{175}$ $ATG_{176}$ $GAK_{177}$ $CCL_{178}$ $GCL_{179}$ $TGK_{180}$ $GAJ_{181}$ $AAJ_{182}$ $XTY_{183}$ $TAK_{184}$ $GGL_{185}$ $GGL_{186}$ $GCL_{187}$ $GTL_{188}$ $CCL_{189}$ wherein A is deoxyadenyl, G is deoxyguanyl, C is deoxycytosyl, T is deoxythymidyl, J is A or G;

K is T or C;

L is A, T, C, or G;

M is A, C, or T;

X is T or C, if the succeeding Y is A or G, and C if the succeeding Y is C or T;

Y is A, G, C, or T, if the preceding X is C, and A or G if the preceding X is T;

W is C or A, if the succeeding Z is G or A, and C if the succeeding Z is C or T;

Z is A, G, C, or T, if the preceding W is C, and A or G if the preceding W is A;

QR is TC, if the succeeding S is A, G, C, or T, and AG if the succeeding S is T or C;

S is A, G, C, or T, if the preceding QR is TC, and T or C if the preceding QR is AG; and subscript numerals refer to the amino acid position in apoaequorin for which the nucleotide sequence corresponds according to the genetic code, the amino acid positions being numbered from the amino end, or a nucleotide sequence coding for a peptide previously mentioned, are also provided for use in carrying out preferred aspects of the invention relating to the production of such pepetides by the techniques of genetic engineering.

BRIEF DESCRIPTION OF THE FIGURES

The accompanying figures and drawings are provided to demonstrate the results obtained in the specific examples which illustrate the invention but are not considered to be limiting thereof.

DESCRIPTION OF THE PREFERRED EMBODIMENTS

Figure 1:
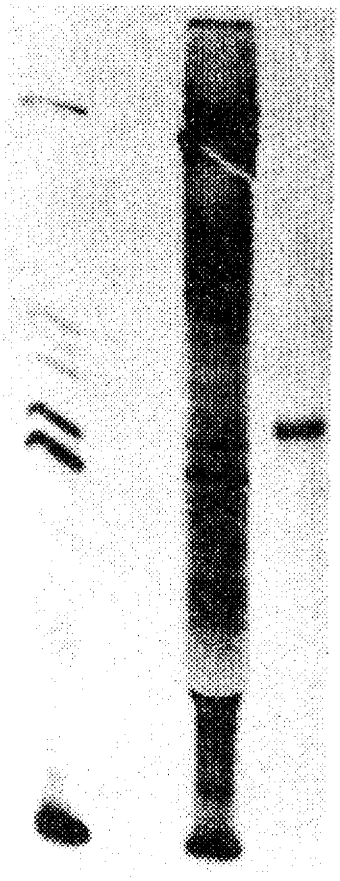
FIG. 1 is a photograph showing an autoradiographic analysis of in vitro translated proteins using poly($A^+$)RNA isolated from Aequorea jellyfish. The translation was performed in the absence (lane 1) or presence (lane 3) of Aequorea poly($A^+$)RNA. The anti-aequorin immunoprecipitated proteins from the two reactions were applied to lanes 2 and 4, respectively. On the right are marked the positions of the protein molecular weight standards phosphorylase b, BSA, ovalbumin, carbonic anhydrase, SBT1 and lysozyme. The position of native aequorin is also indicated.

The present inventor has obtained for the first time recombinant DNA vectors capable of expressing the protein apoaequorin in a microorganism and has additionally identified for the first time the amino acid sequence of apoaequorin, thereby providing access to homogeneous apoaequorin. Using this information a variety of recombinant DNA vectors capable of providing homogeneous apoaequorin in reasonable quantities are obtained. Additional recombinant DNA vectors can be produced using standard techniques of recombinant DNA technology. A transformant expressing apoaequorin has also been produced as an example of this technology.

The amino acid sequence of a typical molecule of apoaequorin is shown in Table 3.

TABLE 3

```
                                                                                              -1
A:                                                                    met thr ser GLU gln tyr ser
B:  ctttgcaccaaaacaccacatcaaatctccagttgataaactaaatcgtcccaacggcaacaggccaac atg acc agc gaa caa tac tca
C:
D:                          30                          60                                   90

                                   10                                         20                                30
val lys leu thr PRO asp phe ASP asn pro LYS trp ile gly arg his lys his met phe asn phe leu |asp val asn his asn gly ARG|
gtc aag ctt aca cca gac ttc gac aac cca aaa tgg att gga cga cac aag cac atg ttt aat ttt ctt |gat gtc aac cac aat gga agg|
    ... ... ... t.. ... ... ... ... ... .g. ... ... ... ... ... ... ..t ... ..c ... ..c ... |... ... ... ... ... ... .aa|
    ... ... ... t.. ... ... ... ... ... .g. ... ... ... ... ... ... ..t ... ..c ... ..c ... |... ... ... ... ... ... .aa|
                                   120                                        150                               180
                                       40                                         50                                60
|ile ser leu asp glu| met val tyr lys ala ser asp ile val ile asn asn leu gly ala thr pro glu gln ala lys arg his lys asp
|atc tct ctt gac gag| atg gtc tac aag gcg tcc gat att gtt ata aac aat ctt gga gca aca cct gaa caa gcc aaa cgt cac aaa gat
|... ... ... ... ...| ... ... ... ... ..a ..t ... ... ..c ..c ..t ..c ... ... ... ... ... ..g ... ... ... ..a ... ... ...
|... ... ... ... ...| ... ... ... ... ..a ..t ... ... ..c ..c ..t ..c ... ... ... ... ... ..g ... ... ... ..a ... ... ...
                                       210                                        240                               270
                                       70                                         80                                90
ala val GLU ALA phe phe gly gly ala gly met lys tyr gly val glu thr GLU trp pro GLU tyr ile glu gly trp lys ARG leu ala
gct gta gaa gcc ttc ttc gga gga gct gga atg aaa tat ggt gta gaa act gaa tgg cct gaa tac atc gaa gga tgg aaa aga ctg gct
... ... ... ... ... ... ... ... ... ... ... ... ... ... ..g ... ... ..t ... ... .c. ..t ..t ... ... ... ... .a. t.. ...
... ... .g. .a. ... ... ... ... ... ... ... ... ... ... ..g ... ... ..t ... ... .c. ... ..t ... ... ... ... .a. t.. ...
                                       300                                        330                               360
                                       100                                        110                               120
SER GLU glu leu LYS ARG tyr SER lys asn GLN ILE thr leu ile arg LEU trp gly asp ala leu phe asp ile ILE |asp lys asp gln|
tcc gag gaa ttg aaa agg tat tca aaa aac caa atc aca ctt att cgt tta tgg ggt gat gca ttg ttc gat atc att |gac aaa gac caa|
a.t ..t ... ... g.g .aa ..c g.c ... ... g.. cca ..g ..c ..c ... a.. ... ... ... ..t ... ..t ... ... g.. |... ... ..t ...|
a.t ..t ... ... g.g .aa ..c g.c ... ... g.. cca ..g ..c ..c ... a.. ... ... ... ..t ... ..t ... ... g.. |... ... ..t ...|
                                       390                                        420                               450
                                       130                                        140                               150
|asn gly ala ile SER leu asp glu| trp lys ala tyr thr lys SER asp gly ile ile gln SER ser glu asp cys glu glu thr phe ARG
|aat gga gct att tca ctg gat gaa| tgg aaa gca tac acc aaa tct gat ggc atc atc caa tcg tca gaa gat tgc gag gaa aca ttc aga
|... ... ..c ... a.. ... ... ...| ... ... ... ... ... ... g.. .c. ..t ... ... ... ..a ... ... ... ... ... ... ... ... ...
|... ... ..c ... a.. ... ... ...| ... ... ... ... ... ... g.. .c. ..t ... ... ... ..a ... ... ... ... ... ... ... ... ...
                                       480                                        510                               540
                                       160                                        170                               180
val cys |asp ile asp glu SER gly gln leu asp val asp glu| met thr arg gln his leu gly phe trp tyr thr met asp pro ala cys
gtg tgc |gat att gat gaa agt gga cag ctc gat gtt gat gag| atg aca aga caa cat tta gga ttt tgg tac acc atg gat cct gct tgc
... ... |... ... ... ... ... ... ..a ... ... ... ... ...| ... ... ... ... ... ... ... ... ... ... ... ... ... ...
... ... |... ... ... ... .a. ... ..a ... ... ... ... ...| ... ... ... ... ... ... ... ... ... ... ... ... ... ...
                                       570                                        600                               630
glu lys leu tyr gly gly ala val pro ...
gaa aag ctc tac ggt gaa gct gtc ccc taa gaaatctgcgg
                                    600
```

Since there is a known and definite correspondence between amino acids in a peptide and the DNA sequence that codes for the peptide, the DNA sequence of a DNA or RNA molecule coding for apoaequorin (or any of the modified peptides later discussed) can readily be derived from this amino acid sequence, and such a sequence of nucleotides is shown in Table 4.

TABLE 4

Nucleotide sequence of one strand of apoaequorin DNA. The numbers refer to the amino acid sequence and corresponding DNA codon sequence beginning at the amino terminus of the protein. The DNA sequence corresponds to the mRNA sequence except that U replaces T in the mRNA.

| | | | | |
|---|---|---|---|---|
| | | | | 5 |
| Val | Lys | Leu | Thr | [Pro or Ser] |
| GTL | AAJ | XTY | ACL | [CCL or QRS] |
| | | | | 10 |
| Asp | Phe | [Asp or Asn] | Asn | Pro |
| GAK | TTK | [GAK or AAK] | AAK | CCL |
| | | | | 15 |
| [Lys or Arg] | Trp | Ile | Gly | Arg |
| [AAJ or WGZ] | TGG | ATM | GGL | WGZ |
| | | | | 20 |
| His | Lys | His | Met | Phe |
| CAK | AAJ | CAK | ATG | TTK |
| | | | | 25 |
| Asn | Phe | Leu | Asp | Val |
| AAK | TTK | XTY | GAK | GTL |
| | | | | 30 |
| Asn | His | Asn | Gly | [Arg or Lys] |
| AAK | CAK | AAK | GGL | [WGZ or AAJ] |
| | | | | 35 |
| Ile | Ser | Leu | Asp | Glu |
| ATM | QRS | XTY | GAK | GAJ |
| | | | | 40 |
| Met | Val | Tyr | Lys | Ala |
| ATG | GTL | TAK | AAJ | GCL |
| | | | | 45 |
| Ser | Asp | Ile | Val | Ile |
| QRS | GAK | ATM | GTL | ATM |
| | | | | 50 |
| Asn | Asn | Leu | Gly | Ala |
| AAK | AAK | XTY | GGL | GCL |
| | | | | 55 |
| Thr | Pro | Glu | Gln | Ala |
| ACL | CCL | GAJ | CAJ | GCL |
| | | | | 60 |
| Lys | Arg | His | Lys | Asp |
| AAJ | WGZ | CAK | AAJ | GAK |
| | | | | 65 |
| Ala | Val | [Glu or Gly] | [Ala or Asp] | Phe |
| GCL | GTL | [GAJ or GGL] | [GCL or GAK] | TTK |
| | | | | 70 |
| Phe | Gly | Gly | Ala | Gly |
| TTK | GGL | GGL | GCL | GGL |
| | | | | 75 |
| Met | Lys | Tyr | Gly | Val |
| ATG | AAJ | TAK | GGL | GTL |
| | | | | 80 |
| Glu | Thr | [Glu or Asp] | Try | Pro |
| GAJ | ACL | [GAJ or GAK] | TGG | CCL |
| | | | | 85 |
| [Glu or Ala] | Tyr | Ile | Glu | Gly |
| [GAJ or GCL] | TAK | ATM | GAJ | GGL |
| | | | | 90 |
| Trp | Lys | [Arg or Lys] | Leu | Ala |
| TGG | AAJ | [WGZ or AAJ] | XTY | GCL |
| | | | | 95 |
| [Ser or Thr] | [Glu, Asp, or Cys] | Glu | Leu | [Lys or Gly] |
| [QRS or ACL] | [GAJ, GAK, or TGK] | GAJ | XTY | [AAJ or GAJ] |
| | | | | 100 |
| [Arg or Lys] | Tyr | [Ser or Ala] | Lys | Asn |
| [WGZ or AAJ] | TAK | [QRS or GCL] | AAJ | AAK |
| | | | | 105 |
| [Gln or Glu] | [Ile or Pro] | Thr | Leu | Ile |
| [CAJ or GAJ] | [ATM or CCL] | ACL | XTY | ATM |
| | | | | 110 |
| Arg | [Leu or Ile] | Trp | Gly | Asp |
| WGZ | [XTY or ATM] | TGG | GGL | GAK |

TABLE 4-continued

Nucleotide sequence of one strand of apoaequorin DNA. The numbers refer to the amino acid sequence and corresponding DNA codon sequence beginning at the amino terminus of the protein. The DNA sequence corresponds to the mRNA sequence except that U replaces T in the mRNA.

| | | | | |
|---|---|---|---|---|
| | | | | 115 |
| Ala | Leu | Phe | Asp | Ile |
| GCL | XTY | TTK | GAK | ATM |
| | | | | 120 |
| [Ile or Val] | Asp | Lys | Asp | Gln |
| [ATM or GTL] | GAK | AAJ | GAK | CAJ |
| | | | | 125 |
| Asn | Gly | Ala | Ile | [Ser or Thr] |
| AAK | GGL | GCL | ATM | [QRS or ACL] |
| | | | | 130 |
| Leu | [Asp] | Glu | Try | Lys |
| XTY | [GAK] | GAJ | TGG | AAJ |
| | | | | 135 |
| Ala | Tyr | Thr | Lys | [Ser or Ala] |
| GCL | TAK | ACL | AAJ | [QRS or GCL] |
| | | | | 140 |
| Ala | Gly | Ile | Ile | Gln |
| GCL | GGL | ATM | ATM | CAJ |
| | | | | 145 |
| [Ser or Thr] | Ser | Glu | [Asp] | Cys |
| [QRS or ACL] | QRS | GAJ | [GAK] | TGK |
| | | | | 150 |
| Glu | Glu | Thr | Phe | Arg |
| GAJ | GAJ | ACL | TTK | WGZ |
| | | | | 155 |
| Val | CYS | Asp | Ile | Asp |
| GTL | TGK | GAK | ATM | GAK |
| | | | | 160 |
| Glu | [Ser or Asn] | Gly | Gln | Leu |
| GAJ | [QRS or AAK] | GGL | CAJ | XTY |
| | | | | 165 |
| Asp | Val | Asp | Glu | Met |
| GAK | GTL | GAK | GAJ | ATG |
| | | | | 170 |
| Thr | Arg | Gln | His | Leu |
| ACL | WGZ | CAJ | CAK | XTY |
| | | | | 175 |
| Gly | Phe | Trp | Tyr | Thr |
| GGL | TTK | TGG | TAK | ACL |
| | | | | 180 |
| Met | Asp | Pro | Ala | Cys |
| ATG | GAK | CCL | GCL | TGK |
| | | | | 185 |
| Glu | Lys | Leu | Tyr | Gly |
| GAJ | AAJ | XTY | TAK | GGL |
| | | | 189 | |
| Gly | Ala | Val | Pro-COOH | |
| GGL | GCL | GTL | CCL | |

Since the DNA sequence of the gene has been fully identified, it is possible to produce a DNA gene entirely by synthetic chemistry, after which the gene can be inserted into any of the many available DNA vectors using known techniques of recombinant DNA technology. Thus the present invention can be carried out using reagents, olasmids, and microorganism which are freely available and in the public domain at the time of filing of this patent application.

For example, nucleotide sequences greater than 100 bases long can be readily synthesized on an Applied Biosystems Model 380A DNA Synthesizer as evidenced by commercial advertising of the same (e.g., Genetic Engineering News, November/December 1984, p. 3). Such obigonucleotides can readily be spliced using, among others, the techniques described later in this application to produce any nucleotide sequence described herein.

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific peptide sequences shown in Table 3, other peptides based on these sequences and representing minor variations thereof will have the biological activity of apoaequorin. For example, up to 15 amino acids can be absent from either or both terminals of the sequence given without losing luciferin and calcium binding ability. Likewise, up to 10 additional amino acids can be present at either or both terminals. These variations are possible because the luciferin and calcium binding sites involve the amino acids in the middle of the given sequences. For example, the luciferin binding site appears to involve amino acids 40–100. Since the terminals are relatively unimportant for biological activity, the identity of added amino acids is likewise unimportant and can be any of the amino acids mentioned herein.

Experimental data is available to verify that added amino acids at the amine terminal do not have a significant effect on bioluminescence. Nevertheless, preferred compounds are those which more closely approach the specific formulas given with 10 or fewer, more preferably 5 or fewer, absent amino acids being preferred for either terminal and 7 or fewer, more preferably 4 or fewer, additional amino acids being preferred for either terminal.

Within the central portion of the molecule, replacement of amino acids is more restricted in order that biological activity can be maintained. However, all of the points of microheterogenity shown in Table 3 or Table 4 represent biologically functional replacements and any combination of the indicated replacements will represent a functional molecule. In both Tables, the main line (Table 3) or first entry (Table 4) represents the more prevelant amino acid or nucleotide for that location and is preferred.

In addition minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the biological activity of the resulting molecule, especially if the replacement does not involve an amino acid at a binding site. Whether a change results in a functioning peptide can readily be determined by incubating the resulting peptide with a luciferin followed by contact with calcium ions. Examples of this process are described later in detail. If light is emitted, the replacement is immaterial, and the molecule being tested is equivalent to those of Table 3. Peptides in which more than one replacement has taken place can readily be tested in the same manner.

DNA molecules that code for such peptides can readily be determined from the list of codons in Table 1 and are likewise contemplated as being equivalent to the DNA sequence of Table 4. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

In addition to the specific nucleotides listed in Table 4, DNA (or corresponding RNA) molecules of the invention can have additional nucleotides preceeding or following those that are specifically listed. For example, poly A can be added to the 3'-terminal, short (e.g., fewer than 20 nucleotides) sequence can be added to either terminal to provide a terminal sequence corresponding to a restriction endonuclease site, stop codons can follow the peptide sequence to terminate transcription, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation of additional DNA from biological sources.

Peptides of the invention can be prepared for the first time as homogeneous preparations, either by direct synthesis or by using a cloned gene as described herein. By "homogeneous" is meant, when referring to a peptide or DNA sequence, that the primary molecular structure (i.e., the sequence of amino acids or nucleotides) of substantially all molecules present in the composition under consideration is identical. The term "substantially" as used in the preceeding sentence preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogenity since the term "homogeneous" relates to the presence of entire moleucles (and fragments thereof) have a single defined structure as opposed to mixtures (such as those that occur in natural apoaequorin) in which several molecules of similar molecular weight are present but which differ in their primary molecular structure. The term "isolated" as used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acylamide gel) but not obtained either as pure substances or as solutions. The term "pure" as used herein preferably has the same numerical limits as "substantially" immediately above. The phrase "replaced by" or "replacement" as used herein does not necessarily refer to any action that must take place but to the peptide that exists when an indicated "replacement" amino acid is present in the same position as the amino acid indicated to be present in a different formula (e.g., when serine is present at position 5 instead of proline).

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

The invention has specifically contemplated each and every possible variation of peptide or nucleotide that could be made by selecting combinations based on the possible amino acid and codon choices listed in Table 3 and Table 4, and all such variations are to be considered as being specifically disclosed.

In a preferred embodiment of the invention, genetic information encoded as mRNA is obtained from Aequorea jellyfish and used in the construction of a DNA gene, which is in turn used to produce a peptide of the invention.

It is preferred to use a cell extract from the light emitting organs of an Aequoria jellyfish as a source of mRNA, although a whole body cell extract may be used. Typically, a jellyfish or parts thereof is cut into small pieces (minced) and the pieces are ground to provide an initial crude cell suspension. The cell suspension is sonicated or otherwise treated to disrupt cell membranes so that a crude cell extract is obtained. Known techniques of biochemistry (e.g., preferential precipitation of proteins) can be used for initial purification if desired. The crude cell extract, or a partially purified RNA portion therefrom, is then treated to further separate the RNA. For example, crude cell extract can be layered on top of a 5 ml cushion of 5.7M CsCl, 10 mM Tris-HCl, pH 7.5, 1 mM EDTA in a 1 in.×3½ in. nitrocellulose tube and centrifuged in an SW27 rotor (Beckman Instruments Corp., Fullerton, Calif.) at 27,000 rpm for 16 hrs at 15° C. After centrifugation, the tube contents are decanted, the tube is drained, and the bottom ½ cm containing the clear RNA pellet is cut off with a razor blade. The pellets are transferred to a flask and dissolved in 20 ml 10 mM Tris-HCl, pH 7.5, 1 mM EDTA, 5% sarcosyl and 5% phenol. The solution is then made 0.1M in NaCl and shaken with 40 ml of a 1:1 phenol:chloroform mixture. RNA is precipitated from the aqueous phase with ethanol in the presence of 0.2M Na-acetate pH 5.5 and collected by centrifugation. Any other method of isolating RNA from a cellular source may be used instead of this method.

Various forms of RNA may be employed such as polyadenylated, crude or partially purified messenger RNA, which may be heterogeneous in sequence and in molecular size. The selectivity of the RNA isolation procedure is enhanced by any method which results in an enrichment of the desired mRNA in the heterodisperse population of mRNA isolated. Any such prepurification method may be employed in preparing a gene of the present invention, provided that the method does not introduce endonucleolytic cleavage of the mRNA.

Prepurification to enrich for desired mRNA sequences may also be carried out using conventional methods for fractionating RNA, after its isolation from the cell. Any technique which does not result in degradation of the RNA may be employed. The techniques of preparative sedimentation in a sucrose gradient and gel electrophoresis are especially suitable.

The mRNA must be isolated from the source cells under conditions which preclude degradation of the mRNA. The action of RNase enzymes is particularly to be avoided because these enzymes are capable of hydrolytic cleavage of the RNA nucleotide sequence. A suitable method for inhibiting RNase during extraction from cells involves the use of 4M guanidium thiocyanate and 1M mercaptoethanol during the cell disruption step. In addition, a low temperature and a pH near 5.0 are helpful in further reducing RNase degradation of the isolated RNA.

Generally, mRNA is prepared essentially free of contaminating protein, DNA, polysaccharides and lipids. Standard methods are well known in the art for accomplishing such purification. RNA thus isolated contains non-messenger as well as messenger RNA. A convenient method for separating the mRNA of eucaryotes is chromatography on columns of oligo-dT cellulose, or other oligonucleotide-substituted column material such as poly U-Sepharose, taking advantage of the hydrogen bonding specificity conferred by the presence of polyadenylic acid on the 3' end of eucaruotic MRNA.

The next step in most methods is the formation of DNA commplementary to the isolated heterogeneous sequences of mRNA. The enzyme of choice for this reaction is reverse transcriptase, although in principle any enzyme capable of forming a faithful complementary DNA copy of the mRNA template could be used. The reaction may be carried out under conditions described in the prior art, using mRNA as a template and a mixture of the four deoxynucleoside triphosphates, dATP, dGTP, dCTP, and dTTP, as precursors for the DNA strand. It is convenient to provide that one of the deoxynucleoside triphosphates be labeled with a radioisotope, for example $^{32}$p in the alpha position, in order to monitor the course of the reaction, to provide a tag for recovering the product after separation procedures such as chromatography and electrophoresis, and for the purpose of making quantitative estimates of recovery. See Efstratiadis, A., et al. supra.

The cDNA transcripts produced by the reverse transcriptase reaction are somewhat heterogeneous with respect to sequences at the 5' end and the 3' end due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and variable length of poly-A region is transcribed depending on the inital binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

The indeterminacy at the 3'-end of the cDNA transcript is due to a variety of factors affecting the reverse transcriptase reaction, and to the possiblity of partial degradation of the RNA template. The isolation of specific cDNA transcripts of maximal length is greatly facilitated if conditions for the reverse transcriptase reaction are chosen which not only favor full length synthesis but also repress the synthesis of small DNA chains. Preferred reaction conditions for avian myeloblastosis virus reverse transcriptase are given in the examples section of U.S. Pat. No. 4,363,377 and are herein incorporated by reference. The specific parameters which may be varied to provide maximal production of long-chain DNA transcripts of high fidelity are reaction temperature, salt concentration, amount of enzyme, concentration of primer relative to template, and reaction time.

The conditions of temperature and salt concentration are chosen so as to optimize specific base-pairing between the oligo-dT primer and the polyadenylated portion of the RNA template. Under properly chosen conditions, the primer will be able to bind at the polyadenylated region of the RNA template, but non-specific initiation due to primer binding at other locations on the template, such as short, A-rich sequences, will be substantially prevented. The effects of temperature and salt are interdependent. Higher temperatures and low salt concentrations decrease the stability of specific base-pairing interactions. The reaction time is kept as short as possible, in order to prevent non-specific initiations and to minimize the opportunity for degradation. Reaction times are interrelated with temperature, lower temperatures requiring longer reaction times. At 42° C., reactions ranging from 1 min. to 10 minutes are suitable. The primer should be present in 50 to 500-fold molar excess over the RNA template and the enzyme should be present in similar molar excess over the RNA template. The use of excess enzyme and primer enhances initiation and cDNA chain growth so that long-chain cDNA transcripts are produced efficiently within the confines of the short incubation times.

In many cases, it will be possible to further purify the CDNA using single-stranded CDNA sequences transcribed from mRNA. However, as discussed below, there may be instances in which the desired restriction enzyme is one which acts only on double-stranded DNA. In these cases, the CDNA prepared as described above may be used as a template for the synthesis of double-stranded DNA, using a DNA polymerase such as reverse transcriptase and a nuclease capable of hydrolyzing single-stranded DNA. Methods for preparing double-stranded DNA in this manner have been described in the prior art. See, for example, Ullrich, A., Shine, J., Chirgwin, J. Pictet, R., Tischer, E., Rutter, W. J. and Goodman, H. M., *Science* (1977) 196:1313.

If desired, the CDNA can be purified further by the process of U.S. Pat. No. 4,363,877, although this is not essential. In this method, heterogeneous cDNA, prepared by transcription of heterogeneous mRNA sequences, is treated with one or two restriction endonucleases. The choice of endonuclease to be used depends in the first instance upon a prior determination that recognition sites for the enzyme exist in the sequence of the cDNA to be isolated. The method depends upon the existence of two such sites. If the sites are identical, a single enzyme will be sufficient. The desired sequence will be cleaved at both sites, eliminating size heterogeneity as far as the desired cDNA sequence is concerned, and creating a population of molecules, termed fragments, containing the desired sequence and homogeneous in length. If the restriction sites are different, two enzymes will be required in order to produce the desired homogeneous length fragments.

The choice of restriction enzyme(s) capable of producing an optimal length nucleotide sequence fragment coding for all or part of the desired protein must be made empirically. If the amino acid sequence of the desired protein is known, it is possible to compare the nucleotide sequence of uniform length nucleotide fragments produced by restriction endonuclease cleavage with the amino acid sequence for which it codes, using the known relationship of the genetic code common to all forms of life. A complete amino acid sequence for the desired protein is not necessary, however, since a reasonably accurate identification may be made on the basis of a partial sequence. Where the amino acid sequence of the desired protein is now known, the uniform length polynucleotides produced by restriction endonuclease cleavage may be used as probes capable of identifying the synthesis of the desired protein in an appropriate in vitro protein synthesizing system. Alternatively, the mRNA may be purified by affinity chromatography. Other techniques which may be suggested to those skilled in the art will be appropriate for this purpose.

The number of restriction enzymes suitable for use depends upon whether single-stranded or double-stranded cDNA is used. The preferred enzymes are those capable of acting on single-stranded DNA, which is the immediate reaction product of mRNA reverse transcription. The number of restriction enzymes now known to be capable of acting on single-stranded DNA is limited. The enzymes HaeIII, HhaI and Hin(f)I are presently known to be suitable. In addition, the enzyme MboII may act on single-stranded DNA. Where further study reveals that other restriction enzymes can act on single-stranded DNA, such other enzymes may appropriately be included in the list of preferred enzymes. Additional suitable enzymes include those specified for double-stranded cDNA. Such enzymes are not preferred since additional reactions are required in order to produce double-stranded cDNA, providing increased opportunities for the loss of longer sequences and for other losses due to incomplete recovery. The use of double-stranded CDNA presents the additional technical disadvantages that subsequent sequence analysis is more complex and laborious. For these reasons, single-stranded cDNA is prefered, but the use of double-stranded DNA is feasible. In fact, the present invention was initially reduced to practice using double-stranded CDNA.

The cDNA prepared for restriction endonuclease treatment may be radioactively labeled so that it may be detected after subsequent separation steps. A preferred technique is to incorporate a radioactive label such as $^{32}P$ in the alpha position of one of the four deoxynucleoside triphosphate precursors. Highest activity is obtained when the concentration of radioactive precursor is high relative to the concentration of the non-radioactive form. However, the total concentration of any deoxynucleoside triphosphate should be greater than 30 μM, in order to maximize the length of cDNA obtained in the reverse transcriptase reaction. See Efstratiadis, A., Maniatis, T., Kafatos, F. C., Jeffrey, A., and Vournakis, J. N., *Cell*, (1975) 4:367. For the purpose of determining the nucleotide sequence of cDNA, the 5' ends may be conveniently labeled with $^{32}P$ in a reaction catalyzed by the enzyme polynucleotide kinase. See Maxam, A. M. and Gilbert, W., *Proc. Natl. Acad. Sci. USA* (1977) 74:560.

Fragments which have been produced by the action of a restriction enzyme or combination of two restriction enzymes may be separated from each other and from heterodisperse sequences lacking recognition sites by any appropriate technique capable of separating polynucleotides on the basis of differences in length. Such methods include a variety of electrophoretic techniques and sedimentation techniques using an ultracentrifuge. Gel electrophoresis is preferred because it provides the best resolution on the basis of polynucleotide length. In addition, the method readily permits quantitative recovery of separated materials. Convenient gel electrophoresis methods have been described by Dingman, C. W., and Peacock, A. C., *Biochemistry* (1968) 7:659, and by Maniatis, T., Jeffrey, A. and van de Sande, H., *Biochemistry* (1975) 14:3787.

Prior to restriction endonuclease treatment, cDNA transcripts obtained fcom most sources will be found to be heterodisperse in length. By the action of a properly chosen restriction endonuclease, or pair of endonucleases, polynucleotide chains containing the desired sequence will be cleaved at the respective restriction sites to yield polynucleotide fragments of uniform length. Upon gel electrophoresis, these will be observed to form a distinct band. Depending on the presence or absence of restriction sites on other sequences, other discrete bands may be formed as well, which will most likely be of different length than that of the desired sequence. Therefore, as a consequence of restriction endonuclease action, the gel electrophoresis pattern will reveal the appearance of one or more discrete bands, while the remainder of the cDNA will continue to be heterodisperse. In the case where the desired cDNA sequence comprises the major polynucleotide species present, the electrophoresis pattern will reveal that most of the cDNA is present in the discrete band.

Although it is unlikely that two different sequences will be cleaved by restriction enzymes to yield fragments of essentially similar length, a method for determining the purity of the defined length fragments is desirable. Sequence analysis of the electrophoresis band may be used to detect impurities representing 10% or more of the material in the band. A method for detecting lower levels of impurities has been developed founded upon the same general principles applied in the initial isolation method. The method requires that the desired nucleotide sequence fragment contain a recognition site for a restriction endonuclease not employed in the initial isolation. Treatment of polynucleotide material, eluted from a gel electrophoresis band, with a restriction endonuclease capable of acting internally upon the desired sequence will result in cleavage of the desired sequence into two sub-fragments, most probably of unequal length. These sub-fragments upon electrophoresis will form two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method. A quantitative measure of the purity of the fragments of desired sequence can be obtained by comparing the relative amounts of material present in those bands representing sub-fragments of the desired sequence with the total amount of material.

Following the foregoing separation or any other technique that isolates the desired gene, the sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. See Sgaramella, V., Van de Sande, J. H., and Khorana, H. G., *Proc. Natl. Acad. Sci. USA* (1970) 67:1468. Where the sequences to be joined are not blunt-ended, the ligase obtained from *E. coli* may be used, Modrich, P., and Lehman, L R., *J. Biol. Chem.* (1970) 245:3626.

The efficiency of reconstituting the original sequence from sub-fragments produced by restriction endonuclease treatment will be greatly enhanced by the use of a method for preventing reconstitution in improper sequence. This unwanted result is prevented by treatment of the homogeneous length cDNA fragment of desired sequence with an agent capable of removing the 5'-terminal phosphate groups on the cDNA prior to cleavage of the homogeneous CDNA with a restriction endonuclease. The enzyme alkaline phosphatase is preferred. The 5'-terminal phosphate groups are a structural prerequisite for the subsequent joining action of DNA ligase used for reconstituting the cleaved sub-fragments. Therefore, ends which lack a 5'-terminal phosphate cannot be covalently joined. The DNA sub-fragments can only be joined at the ends containing a 5'-phosphate generated by the restriction endonuclease cleavage performed on the isolated DNA fragment.

The majority of cDNA transcripts, under the conditions described above, are derived from the mRNA region containing the 5'-end of the mRNA template by specifically priming on the same template with a fragment obtained by restriction endonuclease cleavage. In this way, the above-described method may be used to obtain not only fragments of specific nucleotide sequence related to a desired protein, but also the entire nucleotide sequence coding for the protein of interest. Double-stranded, chemically synthesized oligonucleotide linkers, containing the recognition sequence for a restriction endonuclease, may be attached to the ends of the isolated CDNA, to facilitate subsequent enzymatic removal of the gene portion from the vector DNA. See Scheller et al., *Science* (1977) 196:177. The vector DNA is converted from a continuous loop to a linear form by treatment with an appropriate restriction endonuclease. The ends thereby formed are treated with alkaline phosphatase to remove 5'-phosphate end groups so that the vector DNA may not reform a continuous loop in a DNA ligase reaction without first incorporating a segment of the apoaequorin DNA. The cDNA, with attached linker oligonucleotides, and the treated vector DNA are mixed together with a DNA ligase enzyme, to join the cDNA to the vector DNA, forming a continuous loop of recombinant vector DNA, having the CDNA incorporated therein. Where a plasmid vector is used, usually the closed loop will be the only form able to transform a bacterium. Transformation, as is understood in the art and used herein, is the term used to denote the process whereby a microorganism incorporates extracellular DNA into its own genetic constitution. Plasmid DNA in the form of a closed loop may be so incorporated under appropriate environmental conditions. The incorporated closed loop plasmid undergoes replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used. Once a recombinant vector has been made, transformation of a suitable microorganism is a straightforward process, and novel microorganism strains containing the apoaequorin gene may readily be isolated, using appropriate selection techniques, as understood in the art.

In summary, genetic information can be obtained from Aequorea jellyfish, converted into cDNA, inserted into a vector, used to transform a host microorganism, and expressed as apoaequorin in the following manner:

1. Isolate poly(A+)RNA from Aequorea jellyfish.

2. Synthesize in vitro single-stranded CDNA and then double-stranded cDNA using reverse transcriptase.

3. Digest the single-stranded region with S1 nuclease.

4. Size-fractionate the double-stranded cDNA by gel filtration.

5. Tail the cDNA using terminal transferase and dCTP.

6. Digest pBR322 with PstI and then tail the linear DNA with terminal transferase and dGTP.

7. Anneal the dC-tailed CDNA fragment and dG-tailed pBR322.

8. Transform *E. coli* SK1592. Select for tetracycline resistant colonies.

9. Screen the transformants for ampicillin sensitivity. The $tet^R$ $amp^S$ colonies contain recombinant plasmids. Store them at $-80°$ C.

10. Label an oligonucleotide mixed probe (using a sequence deduced from the determined amino acid sequence) with radioactivity.

11. Grow the members of the Aequorea cDNA bank on nitocellulose filters. Lyse the colonies and fix the DNA to the filters.

12. Hybridize the $^{32}$P-labelled oligonucleotide mixture to the nitrocellulose filters. The $^{32}$P-probe will hybridize to plasmid DNA from those *E. coli* recombinants which contain the aequorin cDNA sequence.

13. Wash excess $^{32}$P-probe from the filters.

14. Expose X-ray film to the filters.

15. Prepare plasmid DNA from the recombinants identified in the Aeguorea CDNA bank.

16. Hybridize the $^{32}$P-labelled oligonucleotide to the plasmid DNA (Southern blot) to confirm the hybridization.

17. Demonstrate that these recombinants contain the aequorin DNA sequence by preparing extracts in EDTA-containing buffers, pH7.2. Charge the expressed apoprotein by adding coelenterate luciferin and β-mercaptoethanol and incubating at 4° C. overnight. A flash of blue light is emitted upon the addition of $Ca^{+2}$ from samples that express aequorin apoprotein.

Although the sequence of steps set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of apoaequorin can be enhanced by including multiple copies of the apoaequorin gene in a transformed host, by selecting a vector known to reproduce in the host, thereby producing large quantities of protein from exogeneous inserted DNA (such as pUC8, ptac12, or pIN-III-ompA1, 2, or 3), or by any other known means of enhancing peptide expression.

In all cases, apoaequorin will be expressed when the DNA sequence is functionally inserted into the vector. By "functionally inserted" is meant in proper reading frame and orientation, as is well understood by those skilled in the art. Typically, an apoaequorin gene will be inserted downstream from a promoter and will be followed by a stop codon, although production as a hybrid protein followed by cleavage may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

All of these patents as well as all other patents and other publications cited in this disclosure are indicative of the level of skill of those skilled in the art to which this invention pertains and are all herein individually incorporated by reference.

The implications of the present invention are significant in that unlimited supplies of apoaequorin will become available for use in the development of luminescent immunoassays or in any other type of assay utilizing aequorin as a marker. Methods of using apoaequorin in a bioluminiscent assay are disclosed in Ser. No. 541,405, filed Oct. 13, 1983, and commonly assigned, which is herein incorporated by reference. Transferring the apoaequorin cDNA which has been isolated to other expression vectors will produce constructs which improve the expression of the apoaequorin polypeptide in *E. coli* or express apoaequorin in other hosts. Furthermore, by using the apoaequorin cDNA or a fragment thereof as a hybridization probe, structurally related genes found in other bioluminescent coelenterates and other organisms such as squid (Mollusca), fish (Pisces), and Crustacea can be easily cloned. These genes include those that code for the luciferases of Renilla, Stylatula, Ptilosarcus, Cavernularia, and Acanthoptilum in addition to those that code for the photoproteins found in the Hydrozoan Obelia and the ctenophores Mnemiopsis and Beroe.

Particularly contemplated is the isolation of genes from these and related organisms that express photoproteins using oligonucleotide probes based on the principal and variant nucleotide sequences disclosed herein. Such probes can be considerably shorter than the entire sequence but should be at least 10, preferably at least 14, nucleotides in length. Longer oligonucleotides are also useful, up to the full length of the gene. Both RNA and DNA probes can be used.

In use, the probes are typically labeled in a detectable manner (e.g., with 32p, $^3H$, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

Particularly preferred are oligonucleotides obtained from the region coding for amino acids 40 through 110 of the peptide sequences described herein, since these are the amino acids involved in binding to luciferin.

Coelenterate luciferin is found in and binds to photoproteins from all the organisms listed in Table 5, and it is contemplated that oligonucleotides as described herein will be useful as probes in isolating photoprotein genes from all these species.

TABLE 5

Distribution of Coelenterate-Type Luciferin

| | |
|---|---|
| 1. Cnidaria (coelenterates) | 4. Pisces |
| A. Anthozoa | *Neoscopelus microchir*[a] |
| Renilla (three sp)[a] | Diaphus |
| Stylatula | |
| Ptilosarcus | 5. Crustacea |
| Cavernularia[b] | A. Decapods (shrimp) |
| Acanthoptilum | *Acanthephyra eximia* |
| B. Hydrozoa | *Acanthephyra purpurea* |
| Aequorea[b] | *Oplophorus spinosus*[a] |
| Obelia | *Heterocarpus grimaldii* |
| | *Heterocarpus laevigatus*[a] |

TABLE 5-continued

| Distribution of Coelenterate-Type Luciferin | |
|---|---|
| 2. Ctenophora | *Systellaspis cristata* |
| Mnemiopsis | *Systellaspis debilis* |
| Beroe | B. Mysidacea (opossum shrimp) |
| | *Gnathophausia ingens* |
| 3. Mollusca | |
| Watasenia (squid)[a] | |

[a]Structure identical to (I) based on chemical and physical data on the extracted luciferins. All others are based on luciferin-luciferase cross reactions as well as on kinetic and bioluminescence emission spectra comparisons.
[b]Additional evidence that the luciferin is identical to (I) is devived from chemical and physical data on the isolated emitter which has been shown to be identical to (II).

The invention now being generally described, it will be more readily understood by reference to the following examples which are included for purposes of illustration only and are not intended to limit the invention unless so stated.

EXAMPLE 1

Purification of Natural Aequorin

Aequorin was purified according to the method of Blinks et al. (J. R. Blinks, P. H. Mattingly, B. R. Jewell, M. van Leeuwen, G. C. Harrer, and D. G. Allen, *Methods Enzymol.* (1978) 57:292–328) except that Sephadex G-75 (superfine) is used in the second gel filtration step. The purification of aequorin took place as follows:

1. Collection of Aeguorea in Friday Harbor, Wash., and removal of circumoral tissue (photocytes).
2. Extraction of proteins from photocytes via hypotonic lysis in EDTA.
3. Ammonium sulfate fractionation of photocyte extract (0–75%).
4. Centrifugation of $(NH_4)_2SO_4$ precipitate; storage at −70° C., during and after shipment from Friday Harbor, Wash.
5. Gel filtration on Sephadex G-50 (fine).
6. Ion-exchange on QAE Sephadex with pH-step and salt gradient elution.
7. Gel filtration on Sephadex G-75 (superfine).
8. Ion-exchange on DEAE-Sephadex with pH-step and salt gradient elution.
9. Lyophilization (in EDTA) of pure aequorin and storage at −80° C. Steps 1–4 were performed at Friday Harbor. Except for collection and removal of circumoral tissue, all steps are done at 0°–40° C. The final product from Step 4 was stored on dry ice in 250 ml centrifuge bottles. The material was shipped in this form.

The purification of aequorin and green fluorescent protein (GFP) was done in Athens, Ga. (Steps 5–9). All steps were performed at 0–40° C. Aequorin-containing fractions were stored at −80° C. between steps; aequorin seems to be stabile to freezing and thawing irrespective of protein concentration.

Step 5: Gel filtration on Sephadex G-50 (fine). Column dimensions: 5.8 cm×97 cm; 2563 ml. The column was run in 10 mM EDTA, pH 5.5 (the disodium salt was used to prepare EDTA solutions) at a flow rate of 75 ml/hour. The GFP and aeqorin eluted together on this column. 65–75% of the aequorin activity was pooled for subsequent purification. Side fractions were also pooled and stored for later purification. Aequorin yield in this step varied from 50% to 80%; 65–75% yields were usually achieved. The capacity of the column was approximately 1000 mg (Bradford) in 75 ml; generally smaller volumes were loaded whenever possible.

Step 6: Ion-exchange on QAE Sephadex. Column dimensions: 5 cm diameter. 5 grams of dry Sephadex were used in this step; the column bed volume changed during chromatography, depending on the ionic strength and composition of the buffer.

Generally the pooled material from 6 to 10 initial G-50 steps was run on this column. Overall yield was improved by doing this, as was efficiency. This step was performed exactly as described by Blinks et al. (1978). After the column was loaded, the GFP was selectively eluted with a pH-step (5 mM Na Ac, 5 mM EDTA, pH 4.75). Aequorin was then eluted in a linear NaCl gradient in 10 mM EDTA, pH 5.5 (500 ml total volume). The GFP was made 10 mM in Tris and the pH raised to 8.0 for storage at −80° until further purification. The aequorin pool was concentrated via ultrafiltration (Amicon YM-10 membrane) in preparation for the next step. Aequorin yield: 80%.

Step 7: Gel filtration on Sephadex G-75 (superfine). Column dimensions: 2.8 cm×150 cm; 924 ml. The column was run in 10 mM EDTA, pH 5.5 at 10 ml/hour. Aequorin yield: 60–80%.

Step 8: Ion-exchange on DEAE-Sephadex. The pooled aequorin from step 7 was run directly onto this column, which was run exactly as the QAE Sephadex column. The aequorin yield was generally 75–80%. This step is unnecessary with most aequorin preps. The material from step 7 is usually pure, according to SDS-PAGE in 12% acrylamide.

Step 9: Aequorin was lyophilized with >95% recovery provided that some EDTA was present. Recoveries varied from 0% to 95% in the absence of EDTA (see Blinks et al., 1978).

EXAMPLE 2

Sequencing Methodology Applied in the Sequence Determination of Aequorin

Amino acid sequence analysis was performed using automated Edman Degradation (Edman and Begg, 1967). The sequence analysis of relatively large amounts of protein or peptide (10 nmol or more) was carried out using a Model 890 B Beckman sequencer (Duke University) updated as described by Brown et al. (1980) and employing a 0.55M Quadrol program with polybrene (Tarr et al., 1978). Two peptides, M3 and M5, which were small or appeared to wash out of the cup with the Quadrol method, were sequenced using a program adapted for dimethylallylamine buffer and polybrene as suggested by Klapper et al. (1978). Phenylthiohydantion (PTH-) derivatives of amino acids were identified using reverse phase HPLC chromatography on a DuPont Zorbay ODS column essentially as described by Hunkapiller and Hood (1978). Peptides which were available at the 2–10 nmol level were sequenced on a Model 890 C Beckman sequencer (University of Washington) using a program for use with 0.1M Quadrol (Brauer et al., 1975) and polybrene. PTH-amino acids were identified using the reverse phase HPLC system described by Ericsson et al. (1977). An applied Biosystems Model 470 A gas phase sequencer (University of Washington) (Hunkapiller et al., 1983) was used for sequence analysis when there was less than 1.5 nmol of peptide available. PTH amino acids from the gas phase instrument were identified using an IBM Cyano column as described by Hunkapiller and Hood (1983).

References

Edman, P. and Begg, G., *Eur. J. Biochem.*, 1, 80–91 (1967).

Brown, A. G., Cornelius, T. U., Mole, J. E., Lynn, J. D., Tidwell, W. A., and Bennett, J. C., *Anal. Biochem.*, 102, 35–38 (1980).

Terr, G. E., Beechner, J. F., Bell, M., and McKean, D. J., *Anal. Biochem.*, 84, 622–627 (1978).

Klapper, D. G., Wilde, C. E., III and Capra, J. D., *Anal. Biochem.*, 85, 126–131 (1978).

Hunkapiller, M. W., and Hood, L. E., *Biochemistry*, 17, 2124–2133 (1978).

Brauer, A. W., Margolies, M. N., and Haber, E., *Biochemistry*, 13, 3029–3035 (1975).

Ericsson, L. H., Wade, R. D., Gagnon, J., McDonald, R. R. and Walsh, K. A. in *Solid Phase Methods in Protein Sequence Analysis* (Previero, A. and ColeHi-Previero, M. A., eds.) pp. 137–142, Elsevier/North Holland, Amsterdam (1977).

Hunkapiller, M. W., Hewick, R. M., Dreyer, W. J., and Hood, L. E., *Methods Enzymol.*, 91, 399–413 (1983).

Hunkapiller, M. W., and Hood, L. E., *Methods Enzymol.*, 91, 486–493 ( 1983) .

EXAMPLE 3

Cloning and Expression of CDNA Coding for Homogeneous Apoaequorin

MATERIALS AND METHODS

Restriction enzymes were purchased from Bethesda Research Laboratories, New England Bio Labs and International Biotechnologies, Inc. and used according to conditions described by the supplier. RNasin and reverse transcriptase were obtained from Biotech and Life Sciences, respectively. Terminal transferase was purchased from PL Biochemicals. Coelecterate luciferin was synthesized as described [Hori, K., Anderson, J. M., Ward, W. W. and Cormier, M. J., *Biochemistry*, 14, 2371–2376 (1975); Hori, K., Charbonneau, H., Hart, R. C., and Cormier, M. J., *Proc. Nat'l. Acad. Sci., USA*, 74, 4285–4287 (1977); Inouye, S., Sugiura, H. Kakoi, H., Hasizuma, K., Goto, T., and Iio, H., *Chem. Lett.*, 141–144 (1975)] and stored as a lyophilized powder until needed.

RNA Isolation and In Vitro Translation

*Aequorea victoria* jellyfish were collected at the University of Washington Marine Biology Laboratory at Friday Harbor, Wash. The circumoral rings were cut from the circumference of the jellyfish and immediately frozen in a dry ice/methanol bath. The tissue was kept at −70° C. until needed.

RNA was isolated according to the method of Kim et al. [Kim, Y-J., Shuman, J., Sette, K., and Przybyla, A., *J. Cell. Biol.*, (1983) 96:393–400] and poly(A)+RNA was prepared using a previously described technique [Aviv and Leder, *PNAS* 69 (1972) 1408–1412].

Poly(A+)RNA (1 pg) and poly($A^-$)RNA (20 μg) were translated using the rabbit reticulocyte in vitro translation system (Pelham and Jackson, *Eur. J. Biochem.* (1976) 247; W. C. Merrick in *Methods in Enz.* 101(c) (1983) 606–615). The lysate was stripped of its endogeneous mRNA with micrococcal nuclease. Each translation (62 μl total volume) was incubated 90 min at 25° C. in the presence of $^{35}$S-methionine (38 μCi). Two μl of each translation were removed for analysis by electrophoresis. Apoaequorin was immunoprecipitated by adding antiaequorin (2 μl) and *Staph aureus* cells to 50 μl of each translation mixture. After several washings the antibody - apoaequorin complex was dissociated by heating in the presence of SDS. The translated products were analyzed on a SDS polyacrylamide (13%) gel. Following electrophoresis the gel was stained with Coomassie R-250 to identify the protein standards and then the gel was impregnated with PPO in DMSO. Fluorography was performed at −70° C.

Recombinant DNA Procedures

Double-stranded cDNA was synthesized from total Aequorea poly($A^+$)RNA as described by Wickens et al., (Wickens, M. P., Buell, G. N., and Schimke, R. T., *J. Biol. Chem.* (1978) 253:2483–2495). After addition of homopolymeric dC tails, double-stranded cDNA was annealed to dG-tailed Pst1-cut pBR322 (Villa-Komaroff, L., Efstradiadis, A., Broome, S., Lomedico, P., Tizard, R., Naber, S. P., Chick, W. L., and Gilbert, *PNAS* (1978) 75:3727–3731) and used to transform *E. coli* strain SK1592. Tetracycline-resistant, ampicillin-sensitive colonies were transferred to and frozen in microtiter dishes at −70° C.

The Aequorea cDNA library was screened for the aequorin CDNA using a synthetic oligonucleotide mixture. The oligonucleotide mixture was supplied by Charles Cantor and Carlos Argarana (Columbia University). Following their purification by polyacrylamide electrophoresis [Maniatis, T., and Efstratidis, A., *Meth. in Enz.* (1980) 65:299–305] and the 17-mers were radioactively labelled using polynucleotide kinase and γ-$^{32}$ P-ATP [Maxam, A. M. and Gilbert, W., *Meth. in Enz.* (1980) 65:499–559]. The unincorporated $^{32}$p was removed by DEAE-cellulose ion-exchange chromatography.

The Aequorea cDNA bank was screened in the following manner: The *E. coli* recombinants were transferred from frozen cultures to nitrocellulose filters (7×11 cm) placed on Luria agar plates. The colonies were grown 12 hours at 37° C. and lysed and then the DNA was fixed as Taub and Thompson [Taub, F., and Thompson, E. B., *Anal. Biochem.* (1982) 126:222–230] described for using Whatman 541 paper. The filters were baked under vacuum for 2 hours after they had been air-dried.

The filters were incubated at 55° C. for 12–20 hours in 3 ml/filter of a prehybridization solution (10× NET, 0.1% SDS, 3× Denhardt's) after first wetting them in 1×SSC. The solution was poured from the hybridization bag and replaced with 1 ml/filter of the hybridization solution (1OXNET, 0.1% SDS, 3× Denhardt's, $1\times10^6$ cpm $^{32}$P-labelled 17-mers per filter). The hybridization was carried out for 24 hours at 37° C. after which the filters were washed four times in 10×SSC at 4° C. for 10 min. The filters were air dried and then wrapped in plastic wrap. Kodak XAR-film was exposed to the filters at −70° C. using a DuPont Cronex intensifying screen.

Growth and Extraction Procedures for *E. coli*

*E. coli* SK1592 containing pAEQ1 - pAEQ6 were grown overnight in 25 ml of Luria broth at 37° C. The cells were centrifuged and then resuspended in 5 ml of 10% sucrose, 50 mM Tris pH 8. The cells were lysed with the addition of the following: 7.2 μl of 0.1M phenylmethylsulfonylfluoride, 312 μl of 0.2M EDTA, 10 mg lysozyme, and 10 μl of 10 mg/ml RNase A. After 45 min on ice, the mixture was centrifuged at 43,500 ×g for one hour. The supernatent was saved.

Purification and Assay of Aequorin

Aequorin was extracted and purified by the method of Blinks et al. [Blinks, J. R., Wier, W. G., Hess, P., and Prendergast, F. G., *Prog. Biophys. Molec. Biol* (1982) 40:1–114]. Aequorin, or photoprotein activity, was measured by injecting 5 μl of the sample into 0.5 ml of 0.1M $CaC_2$, 0.1M Tris, pH 8.0 and simultaneously measuring peak light intensity and total photons. The design of photometers for making such measurements and calibrating the instrument for absolute photon yields have been previously described [Anderson, J. M. Faini, G. J., and Wampler, J. E., *Methods in Enz.* (1978) 57:529–559; Charbonneau, H., and Cormier, M. J., *J. Biol. Chem.* (1979) 254:769–780].

Partial Purification of Apoaequorin Activity in pAEQ1 Extracts

The expressed apoaequorin was partially purified by passage of 23 ml of a pAEQ1 extract over a 42 ml bed volume of Whatman DE-22 equilibrated in 1 mM EDTA, 1.5 mM Tris, pH 7.5. An 800 ml NaCl gradient (0–1M) was applied and the active apoaequorin eluted at 0.3M NaCl. The peak fractions were pooled and dialyzed against 0.5M KCl, 10 mM EDTA, and 15 mM Tris, pH 7.5 for the experiments described in FIG. 3.

RESULTS AND DISCUSSION

In Vitro Translation of Aequorea poly($A^+$)RNA

Approximately 1.6 μg poly($A^+$)RNA was isolated from each gram of frozen jellyfish tissue. The results of the in vitro translation of the Aequorea poly($A^+$)RNA are shown in FIG. 1. The translation products which reacted with anti-aequorin are shown in lane 4. The $^{35}S$ counts immunoprecipitated represented 0.3% of the total acid-precipitable counts in the translation which implies that the apoaequorin mRNA represents approximately 0.3% of the total poly($A^+$)mRNA populations. This relative abundance agrees well with the fraction of total protein (0.5%) which corresponds to aequorin in a crude extract of circumoral rings from Aequorea. No proteins were immunoprecipitated when the in vitro translation was performed in the absence of Aequorea RNA (lane 2) or in the presence of Aequorea poly($A^-$) RNA (data not shown).

Figure 4:
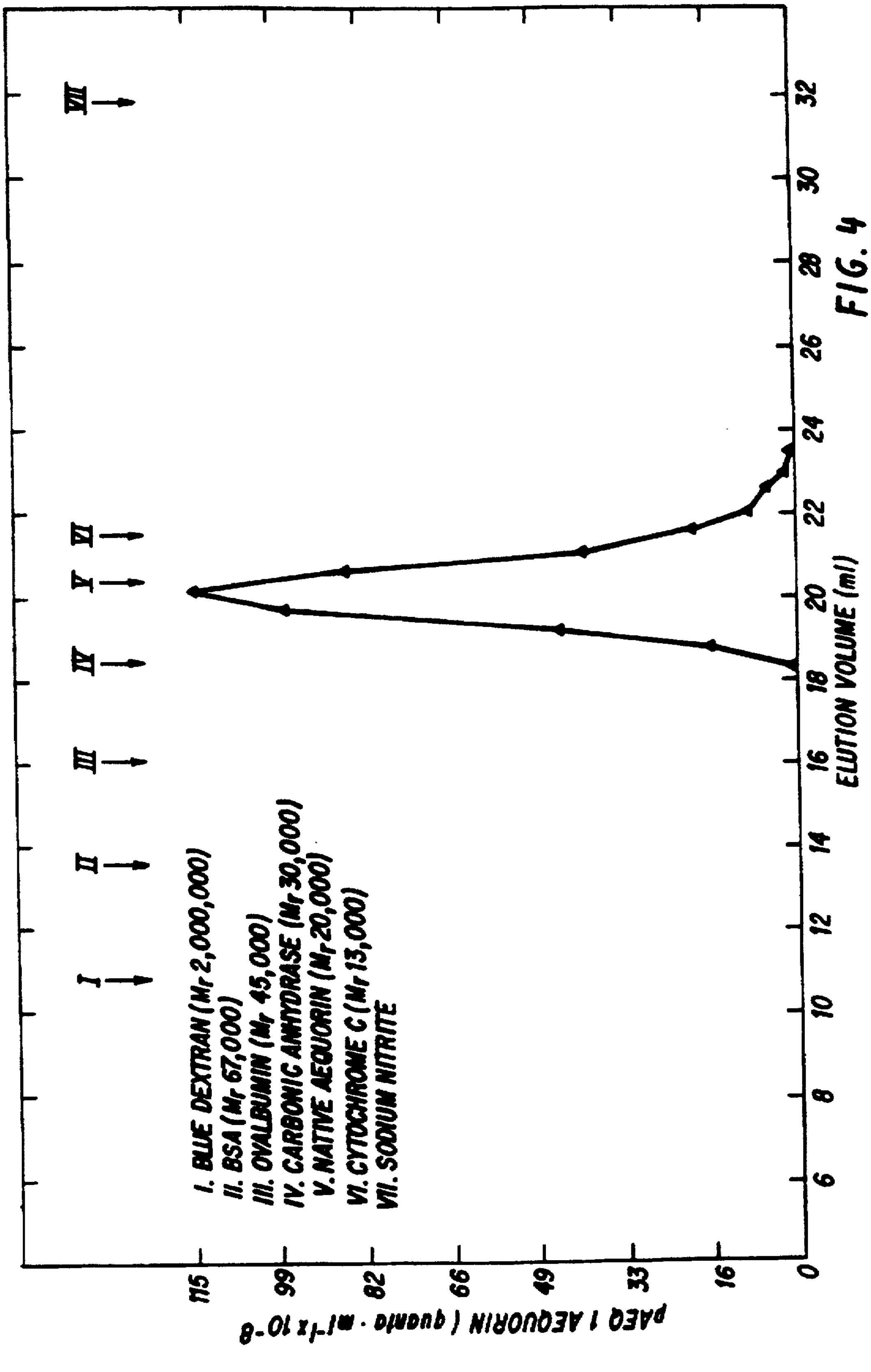
FIG. 4 is a graph of a gel filtration profile of the $Ca^{2+}$-dependent photoprotein activity generated from pAEQ1 extracts. Partially purified apoaequorin activity from PAEQI extracts were used to generate $Ca^{2+}$-dependent photoprotein activity as described in FIG. 3. This photoprotein fraction (50 µl) was then placed on a G-75-40 superfine column (30.7 ml bed volume) equilibrated with 10 mM EDTA, 15 mM Tris, pH 7.5 and 100 mM KCL. The elution positions of various molecular weight markers are indicated.

The primary translation products immuno-precipitated with the anti-aequorin migrated on the SDS-PAGE gel with an apparent molecular weight (23,400 daltons, lane 4) slightly greater than that for native aequorin isolated from Aequorea (22,800 daltons, indicated in FIG. 1). This data, and the data shown in FIG. 4, are consistent with the presence of a presequence of approximately seven additional amino acids at the amino terminal of the primary translation product.

The proteins immunoprecipitated from the poly($A^+$)RNA translation migrated as a doublet or even a triplet (lane 4, FIG. 1) if one studies the original autoradiogram. This result can be interpreted in two ways. Firstly, multiple apoaequorin genes may exist in *Aequorea victoria* and their respective preproteins differ in molecular weight due to various lengths of their presequences. Aequorin isozymes [Blinks, J. R., and Harrer, G. C., *Fed. Proc.* (1975) 34:474] may be indicative of such a multi-gene family. Secondly, the *Aequorea victoria* population at Friday Harbor may consist of several species of Aequorea.

The Aequorea CDNA library used contained 6000 recombinants having inserts greater than 450 bp. Of 25 random recombinants screened, none had inserts less than 500 bp and two were larger than 3 kbp.

The Aequorea CDNA bank was screened with the following mixed synthetic oligonucleotide probe:

```
       A  A      A
3'-ACCAT TGGTACCT GG-5'
       C  T      G
          C
```

The DNA sequences of these oligonucleotides were determined by an examination of the complete amino acid sequence of apoaequorin. These oligonucleotides are complementary to the mRNA which codes for the peptide $Trp^{173}$.Tyr.Thr.Met.Asp.$Pro^{178}$ in the carboxy terminus-region of the aequorin polypeptide. The 17-mers were $^{32}P$-labeled and hybridized to plasmid DNA from the Aequorea CDNA library as described in Methods.

Figure 2:
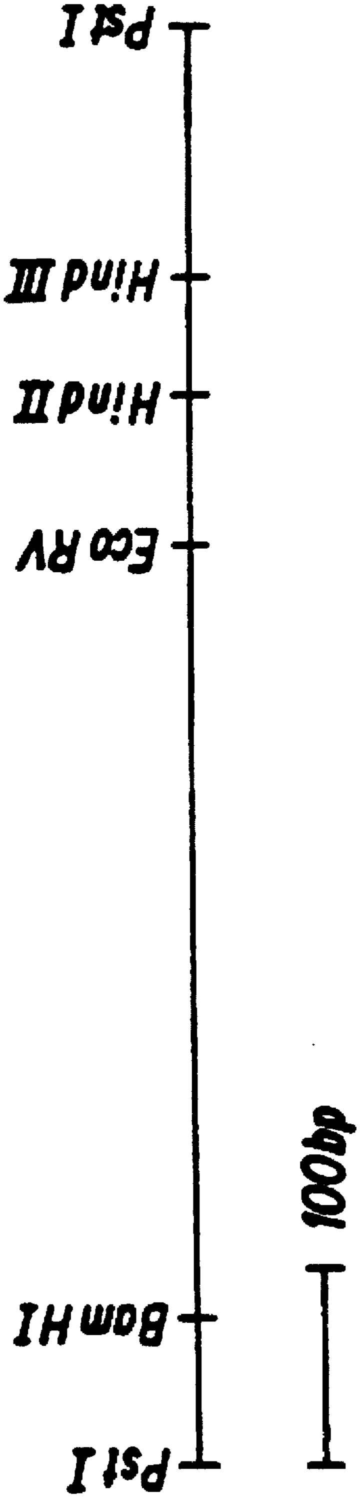
FIG. 2 is a restriction map of a gene isolated from an *Aqueous victoria* jellyfish that contains a DNA sequence coding for apoaequorin.

Six transformants were identified which contained plasmids having inserts that hybridized to the synthetic oligonucleotides. The restriction map of the plasmid containing the largest Pst I insert, pAEQ1, is shown in FIG. 2. No hybridization of the synthetic oligonucleotides would occur if pAEQ1 was digested with BamHI. Upon examination of the 17-mers DNA sequence, the hybridization probe does contain a BamHI recognition sequence (GGATCC). Hence, the BamHI site in pAEQ1 could be used to identify the 3'-region of the apoaequorin coding sequence. The recombinant plasmid pAEQ1 does indeed contain the apoaequorin cDNA as demonstrated by its expression in *E. coli*, as described below.

Expression of Apoaequorin in *E. coli*

In order to find out whether any of these six transformants were expressing biologically active apoaequorin, extracts of each of these, as well as the host strain, were prepared as described in Methods. To. 0.5 ml of each extract was added β-mercaptoethanol (2 mM) and coelenterate luciferin (0.1 mM) and the mixture allowed to incubate at 40 for 20 hours. This mixture was then assayed for $Ca^{2+}$-dependent photoprotein activity as described in Methods. $Ca^{2+}$-dependent luminescence was observed in extracts prepared from the recombinant pAEQ1, but no such luminescence was observed in extracts of the host strain or in extracts derived from any of the other transformants. The inserts in pAEQ1–6 cross hybridized suggesting that they contain homologous DNA sequences. However, if the cDNA inserts in pAEQ2–6 were not of sufficient length or oriented improperly within the plasmid, apoaequorin activity in those extracts would not be expected.

Figure 3:
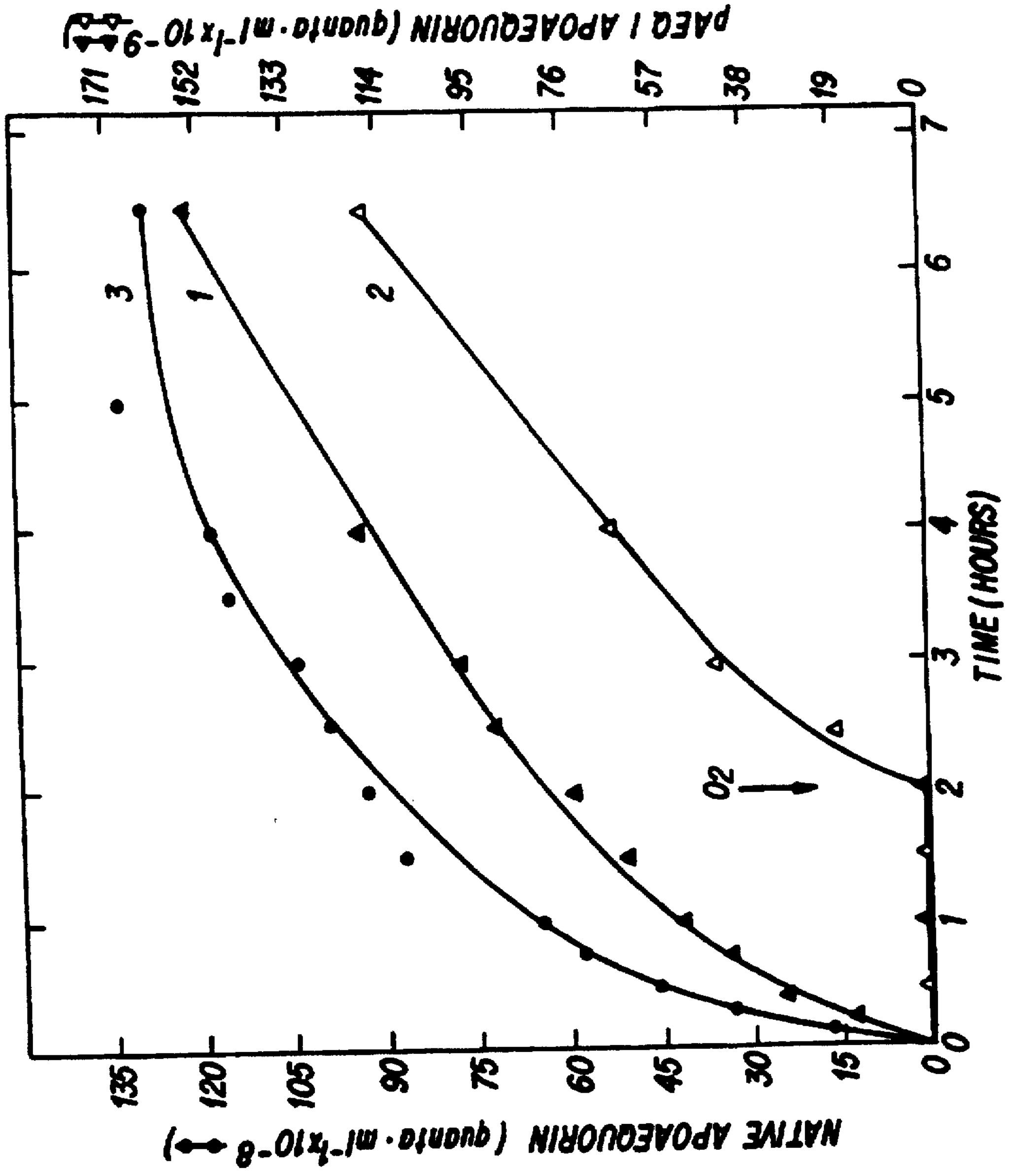
FIG. 3 is a graph of time- and oxygen-dependent formulation of $Ca^{2+}$-dependent photoprotein activity in pAEQ1 extracts. Conditions used: (a) In curves 1 and 2, 0.5 ml aliquotes of the active fractions were made 2 mM in β-mercaptoethanol and 0.1 mM in coelenterate luciferin and incubated at 4° for the times indicated. At appropriate time intervals, 5 µl aliquotes were removed and assayed for photoprotein activity. (b) In curve 2, dissolved $O_2$ levels were reduced by bubbling with Ar gas and the mixture exposed to oxygen at the time indicated. (c) In curve 3, native apoaequorin was used in the incubation mixture in place of the pAEQ1 extract.

The kinetics of formation of photoprotein activity from extracts of pAEQ1 are similar to that observed with native, mixed apoaequorin as shown in FIG. 3. Requirements for the formation of photoprotein activity in this extract is also identical to that observed when authentic apoaequorin is used. As FIG. 3 shows, dissolved $O_2$ is required. Furthermore, the elimination of either β-mercaptoethanol or coelenterate luciferin from the reaction mixture results in zero production of $Ca^{2+}$-dependent photoprotein activity. Injection of the active commponent into $Ca^{2+}$-free buffers produced no luminescence. The subsequent addition of $Ca^{2+}$ resulted in a luminescence flash.

To further characterize the active component in extracts of pAEQ1, this recombinant plasmid was subjected to chromatography over DE-22 as described in Methods. The apoaequorin activity eluted at about 0.3M salt which is similar to that observed for authentic apoaequorin. The active fractions were then incubated in the presence of coelenterate luciferin, β-mercaptoethanol and oxygen to generate photoprotein activity as described in FIG. 3. This mixture was then subjected to gel filtration. As FIG. 4 shows, the photoprotein activity generated from the partially purified component in pAEQ1 extracts eluted from the column with an $M_r$ of 20,600 as compared to a value of 19,600 for native aequorin. Similar results were observed during in vitro translation experiments (FIG. 1). From the data of FIG. 4, one may also conclude that the luciferin becomes tightly associated with the active component in pAEQI extracts under the charging conditions used.

The pooled photoprotein fraction from FIG. 4 produces a luminescence flash upon the addition of $Ca^{2+}$. The kinetics of this flash was indistinguishable from the kinetics of the $Ca^{2+}$-dependent aequorin reaction. Other recombinant plasmids did not express a light-emitting protein when present in transformants, as is shown in Table 6 below.

The above data show that the CDNA inserted into pAEQ1 represents the full-length cDNA coding for apoaequorin. The data also show that this CDNA is being expressed in pAEQ1 and that the protein product is indistinguishable in its biological properties from that of native, mixed apoaequorin. The level of expression was estimated to be about 0.01% of the total soluble protein.

TABLE 6

Recharging of Apoaequorin in Extracts of Apoaequorin cDNA Clones

| Clone | Peak Light Intensity (hv sec$^{-1}$) in Extracts +$Ca^{2+}$ | -$Ca^{2+}$ |
|---|---|---|
| pAEQ1 | 5 × 10$^6$ | 0 |
| pAEQ1 | 0 | 0 |
| pAEQ3 | 0 | 0 |
| pAEQ4 | 0 | 0 |
| pAEQ5 | 0 | 0 |
| pAEQ6 | 0 | 0 |
| SK 1592 (Host Strain) | 0 | 0 |

To 0.5 ml of each extract was added mercaptoethanol (2 mM) and coelenterate luciferin (0.015 mM). The mixture was incubated at 4° for 20 hours. A 5 μl sample was removed, injected into 0.5 ml of 0.1 mM $Ca^{2+}$, and peak light intensity measured.

The invention now being fully described, it will be apparent to one of ordinary skill in the art that many changes and modifications can be made thereto without departing from the spirit or scope of the invention as set forth herein.

What is claimed is:

1. An isolated apoaequorin polypeptide sequence comprising,

VAL LYS LEU THR SER ASP PHE ASP ASN PRO ARG TRP
ILE GLY ARG HIS LYS HIS MET PHE ASN PHE LEU ASP
VAL ASN HIS ASN GLY LYS ILE SER LEU ASP GLU MET
VAL TYR LYS ALA SER ASP ILE VAL ILE ASN ASN LEU
GLY ALA THR PRO GLU GLN ALA LYS ARG HIS LYS ASP
ALA VAL GLU ALA PHE PHE GLY GLY ALA GLY MET LYS
TYR GLY VAL GLU THR ASP TRP PRO ALA TYR ILE GLU
GLY TRP LYS LYS LEU ALA THR ASP GLU LEU GLU LYS
TYR ALA LYS ASN GLU PRO THR LEU ILE ARG ILE TRP
GLY ASP ALA LEU PHE ASP ILE VAL ASP LYS ASP GLN
ASN GLY ALA ILE THR LEU ASP GLU TRP LYS ALA TYR
THR LYS ALA ALA GLY ILE ILE GLN SER SER GLU ASP
CYS GLU GLU THR PHE ARG VAL CYS ASP ILE ASP GLU
SER GLY GLN LEU ASP VAL ASP GLU MET THR ARG GLN
HIS LEU GLY PHE TRP TYR THR MET ASP PRO ALA CYS
GLU LYS LEU TYR GLY GLY ALA VAL PRO.

2. The polypeptide sequence of claim 1 wherein said polypeptide is capable of producing light when combined with a luciferin and contacted with calcium ions.

* * * * *